United States Patent
Church

(10) Patent No.: US 10,273,312 B2
(45) Date of Patent: Apr. 30, 2019

(54) **ANTIBODY SPECIFIC TO *STAPHYLOCOCCUS AUREUS*, THERAPEUTIC METHOD AND DETECTION METHOD USING SAME**

(71) Applicant: William R Church, Burlington, VT (US)

(72) Inventor: William R Church, Burlington, VT (US)

( * ) Notice: Subject to any disclaimer, the term of this patent is extended or adjusted under 35 U.S.C. 154(b) by 0 days.

(21) Appl. No.: 16/027,538

(22) Filed: Jul. 5, 2018

(65) Prior Publication Data

US 2018/0371108 A1    Dec. 27, 2018

Related U.S. Application Data

(60) Continuation of application No. 15/583,384, filed on May 1, 2017, now Pat. No. 10,023,655, which is a continuation of application No. 15/155,209, filed on May 16, 2016, now Pat. No. 9,637,555, which is a division of application No. 14/604,521, filed on Jan. 23, 2015, now Pat. No. 9,353,189.

(60) Provisional application No. 61/931,236, filed on Jan. 24, 2014.

(51) Int. Cl.
| | |
|---|---|
| *C07K 16/40* | (2006.01) |
| *C07K 16/36* | (2006.01) |
| *C07K 16/12* | (2006.01) |
| *A61K 39/00* | (2006.01) |

(52) U.S. Cl.
CPC .......... *C07K 16/40* (2013.01); *C07K 16/1271* (2013.01); *C07K 16/36* (2013.01); *A61K 2039/505* (2013.01); *C07K 2317/24* (2013.01); *C07K 2317/55* (2013.01); *C07K 2317/565* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | | |
|---|---|---|---|---|
| 6,299,879 | B1 * | 10/2001 | Boden Wastfalt | C07K 14/31 424/130.1 |
| 9,353,189 | B2 * | 5/2016 | Church | C07K 16/40 |
| 9,637,555 | B2 * | 5/2017 | Church | C07K 16/40 |
| 10,023,655 | B1 * | 7/2018 | Church | C07K 16/40 |

* cited by examiner

*Primary Examiner* — Jennifer E Graser

(57) ABSTRACT

We provide new monoclonal antibody inhibitors of coagulases for treatment of *S. aureus*. The monoclonal antibodies are useful in targeting the SC N-terminus and inhibiting SC-ProT activation. The monoclonal antibodies are able to bind to and interfere with, modulate, and/or inhibit the binding interactions between the staphylocoagulase protein and its ligand protein prothrombin in blood and tissues. The antibodies are effective in inhibiting the activation of prothrombin.

5 Claims, 35 Drawing Sheets

Specification includes a Sequence Listing.

| Mutated Peptide Ala 8 | I | V | T | K | D | Y | S | A | E | S |
| Mutated Peptide Ala 9 | I | V | T | K | D | Y | S | K | A | S |
| Mutated Peptide Ala 8 & 9 | I | V | T | K | D | Y | S | A | A | S |

Figure 13

|  | Parameters | GMA-2105 | GMA-2105$_{Chimera}$ |
|---|---|---|---|
| Probe SC(1-246) S7C-BodipyFL | Stoichiometry (mol mAb / mol probe) | 0.99 ± 0.07 | 0.94 ± 0.06 |
|  | $K_D$ (nM) | 1.09 ± 0.25 | 0.79 ± 0.40 |
| Competitor Wild Type SC(1-246) | Stoichiometry (mol mAb / mol wild type) | 1.20 ± 0.14 | 1.35 ± 0.09 |
|  | $K_D$ (nM) | 0.71 ± 0.32 | 0.75 ± 0.44 |

Figure 30

SEQUENCE LISTING

```
<160> NUMBER OF SEQ ID NOS: 27

<210> SEQ ID NO 1
<211> LENGTH: 2067
<212> TYPE: DNA
<213> ORGANISM: Staphylococcus aureus

<400> SEQUENCE: 1
atagtaacaa aggattatag caaagagtca agagtgaatg agaacagtaa atatgggaca      60
ttaatttcag actggtattt aaaagggaga ttaactagtc tagaatctca atttatcaat     120
gcattggata ttttagagac atatcattat ggcgaaaaag agtataaaga tgcaaaagat     180
aaattgatga caagaatttt aggggaagac caataccttt tagaaagaaa aaaagtgcag     240
tatgaggaat acaaaaaatt ataccaaaaa tataagaag agaatccaac ctctaaagtt     300
aaaatgaaaa cattcgatca atatacaata gaagatttaa ctatgaggga atataatgag     360
ttaacagaat cattaaaaag tgctgtaaaa gactttgaga aagatgttga aaaaatagaa     420
aatcaacatc atgatttgaa accatttact gatgaaatgg aagagaaggc tacttctaga     480
gttgatgatt tagcaaataa agcatatagt gtttattttg catttgttag ggatacacaa     540
cataaaactg aggcattaga gttaaaagcg aaagtagatt tagttttagg tgatgaggat     600
aaaccgcatc gtatttctaa tgaaagaatt gaaaagaaa tgataaaaga tttagaatct     660
attattgaag atttctttat agaaactggt ttaaataagc ctggtaatat tacgagttat     720
gatagtagta aacatcacta taaaaatcac agtgaaggtt ttgaggctct agtcaaagaa     780
acaagagaag cagtagcaaa cgctgacgaa tcttggaaaa ctaaaactgt aaaaaaatac     840
ggtgaatctg aaacaaaatc tcctgttgta aaagaagaga caaagttga agaccctcaa     900 tcacctaaat ttgataacca acaagaggtt aaaactacgg ctggtaaagc tgaagaaaca     960
acacaaccag ttgcacaacc attagttaaa attccacagg gcacaattac aggtgaaatt    1020
gtgaaaggtc cggaatatcc aacgatggaa aataaaacgt tacaaggtga aatcgttcaa    1080
ggtccagatt tcccaacaat ggaacaaagc ggtccatctt taagcgacaa ttatactcaa    1140
ccgacgacac cgaaccctat tttagaaggt cttgaaggta gctcatctaa acttgaaata    1200
aaaccacaag gtactgaatc aacgttgaaa ggtattcaag gagaatcaag tgatattgaa    1260
gttaaacctc aagcaactga aacaacagaa gcttctcaat atggtccgag accgcaattt    1320
aacaaaacac ctaagtatgt gaaatataga gatgctggta caggtattcg tgaatacaac    1380
gatggaacat ttggatatga agcgagacca agattcaaca agccatcaga aacaaacgca    1440
tacaacgtaa cgacaaatca agatggcaca gtatcatacg gcgcccgccc aacacaaaac    1500
aaggcatcag aaacaaacgc atataacgta acaacacatg caaacggcca agtatcatac    1560
ggagctcgcc caacacaaaa gaagccaagc gaaacaaatg catataacgt aacaacacat    1620
```

```
gcaaacggcc aagtatcata tggcgcccgc ccgacataca acaagccaag cgaaacaaat   1680
gcatataacg taacaacaca cggaaatggc caagtatcat atggagctcg tccgacatac   1740
aagaaaccaa gtaaacaaa tgcatataac gtaacaacac atgcaaacgg ccaagtgtca    1800
tacggagctc gcccaacaca aaagaagcca agcgaaacaa acgcatataa cgtaacaaca   1860
catgcaaatg ccaagtatc atacggagct cgcccaacac aaaagaagcc aagcgaaaca    1920
aacgcatata acgtaacaac acacggaaac ggtcaagtgt catacggcgc tcgtccgaca   1980
tacaacaagc caagtaaaac aaatgcatac aatgtaacaa cacatgcaga tggtactgcg   2040
acatatggtc ctagagtaac aaaataa                                       2067

<210> SEQ ID NO 2
<211> LENGTH: 689
<212> TYPE: PRT
<213> ORGANISM: Staphylococcus aureus

<400> SEQUENCE: 2

Ile Val Thr Lys Asp Tyr Ser Lys Glu Ser Arg Val Asn Glu Asn Ser
1               5                   10                  15

Lys Tyr Gly Thr Leu Ile Ser Asp Trp Tyr Leu Lys Gly Arg Leu Thr
            20                  25                  30

Ser Leu Glu Ser Gln Phe Ile Asn Ala Leu Asp Ile Leu Glu Thr Tyr
        35                  40                  45

His Tyr Gly Glu Lys Glu Tyr Lys Asp Ala Lys Asp Lys Leu Met Thr
    50                  55                  60

Arg Ile Leu Gly Glu Asp Gln Tyr Leu Leu Glu Arg Lys Lys Val Gln
65                  70                  75                  80

Tyr Glu Glu Tyr Lys Lys Leu Tyr Gln Lys Tyr Lys Glu Glu Asn Pro
                85                  90                  95

Thr Ser Lys Gly Leu Lys Leu Lys Thr Phe Asp Gln Tyr Thr Ile Glu
            100                 105                 110

Asp Leu Thr Met Arg Glu Tyr Asn Glu Leu Thr Glu Ser Leu Lys Ser
        115                 120                 125

Ala Val Lys Asp Phe Glu Lys Asp Val Glu Lys Ile Glu Asn Gln His
    130                 135                 140

His Asp Leu Lys Pro Phe Thr Asp Glu Met Glu Glu Lys Ala Thr Ser
145                 150                 155                 160

Arg Val Asp Asp Leu Ala Asn Lys Ala Tyr Ser Val Tyr Phe Ala Phe
                165                 170                 175

Val Arg Asp Thr Gln His Lys Thr Glu Ala Leu Glu Leu Lys Ala Lys
            180                 185                 190

Val Asp Leu Val Leu Gly Asp Glu Asp Lys Pro His Arg Ile Ser Asn
        195                 200                 205

Glu Arg Ile Glu Lys Glu Met Ile Lys Asp Leu Glu Ser Ile Ile Glu
    210                 215                 220

Asp Phe Phe Ile Glu Thr Gly Leu Asn Lys Pro Gly Asn Ile Thr Ser
225                 230                 235                 240

Tyr Asp Ser Ser Lys His His Tyr Lys Asn His Ser Glu Gly Phe Glu
                245                 250                 255

Ala Leu Val Lys Glu Thr Arg Glu Ala Val Ala Asn Ala Asp Glu Ser
            260                 265                 270

Trp Lys Thr Lys Thr Val Lys Lys Tyr Gly Glu Ser Glu Thr Lys Ser
        275                 280                 285

Pro Val Val Lys Glu Glu Asn Lys Val Glu Asp Pro Gln Ser Pro Lys
```

```
        290                 295                 300
    Phe Asp Asn Gln Gln Glu Val Lys Thr Thr Ala Gly Lys Ala Glu Glu
    305                 310                 315                 320

Thr Thr Gln Pro Val Ala Gln Pro Leu Val Lys Ile Pro Gln Gly Thr
                    325                 330                 335

Ile Thr Gly Glu Ile Val Lys Gly Pro Glu Tyr Pro Thr Met Glu Asn
                340                 345                 350

Lys Thr Leu Gln Gly Glu Ile Val Gln Gly Pro Asp Phe Pro Thr Met
    355                 360                 365

Glu Gln Ser Gly Pro Ser Leu Ser Asp Asn Tyr Thr Gln Pro Thr Thr
    370                 375                 380

Pro Asn Pro Ile Leu Glu Gly Leu Glu Gly Ser Ser Lys Leu Glu
    385                 390                 395                 400

Ile Lys Pro Gln Gly Thr Glu Ser Thr Leu Lys Gly Ile Gln Gly Glu
                405                 410                 415

Ser Ser Asp Ile Glu Val Lys Pro Gln Ala Thr Glu Thr Thr Glu Ala
                420                 425                 430

Ser Gln Tyr Gly Pro Arg Pro Gln Phe Asn Lys Thr Pro Lys Tyr Val
    435                 440                 445

Lys Tyr Arg Asp Ala Gly Thr Gly Ile Arg Glu Tyr Asn Asp Gly Thr
    450                 455                 460

Phe Gly Tyr Glu Ala Arg Pro Arg Phe Asn Lys Pro Ser Glu Thr Asn
    465                 470                 475                 480

Ala Tyr Asn Val Thr Thr Asn Gln Asp Gly Thr Val Ser Tyr Gly Ala
                485                 490                 495

Arg Pro Thr Gln Asn Lys Ala Ser Glu Thr Asn Ala Tyr Asn Val Thr
                500                 505                 510

Thr His Ala Asn Gly Gln Val Ser Tyr Gly Ala Arg Pro Thr Gln Lys
    515                 520                 525

Lys Pro Ser Glu Thr Asn Ala Tyr Asn Val Thr Thr His Ala Asn Gly
    530                 535                 540

Gln Val Ser Tyr Gly Ala Arg Pro Thr Tyr Asn Lys Pro Ser Glu Thr
    545                 550                 555                 560

Asn Ala Tyr Asn Val Thr Thr His Gly Asn Gly Gln Val Ser Tyr Gly
                565                 570                 575

Ala Arg Pro Thr Tyr Lys Lys Pro Ser Lys Thr Asn Ala Tyr Asn Val
                580                 585                 590

Thr Thr His Ala Asn Gly Gln Val Ser Tyr Gly Ala Arg Pro Thr Gln
    595                 600                 605

Asn Lys Pro Ser Glu Thr Asn Ala Tyr Asn Val Thr Thr His Ala Asn
    610                 615                 620

Gly Gln Val Ser Tyr Gly Ala Arg Pro Thr Gln Asn Lys Pro Ser Glu
    625                 630                 635                 640

Thr Asn Ala Tyr Asn Val Thr Thr His Gly Asn Gly Gln Val Ser Tyr
                645                 650                 655

Gly Ala Arg Pro Thr Tyr Asn Lys Pro Ser Lys Thr Asn Ala Tyr Asn
    660                 665                 670

Val Thr Thr His Ala Asp Gly Thr Ala Thr Tyr Gly Pro Arg Val Thr
    675                 680                 685

Lys

<210> SEQ ID NO 3
<211> LENGTH: 873
```

```
<212> TYPE: DNA
<213> ORGANISM: Staphylococcus aureus

<400> SEQUENCE: 3
gtagtaccag aaacaggtat taataaaata attccagatt atgataaata taagaatgca      60
ctaaagctaa atgtgagtag tttaactaac aacaataact ttgtagcttc tgaagataaa     120
ttgaaaaaaa ttgcagatcc atcagcagct ggtaaaattg taggtggaaa atttgccgta     180
ctagaatcaa agttaggaag tattgtacca gagtacaaag aaataaataa acgtgcgaat     240
gtaacaggaa acaacaatcc cagtcataat attggaaagt cttttgttac taaaggtcca     300
gaagtaaaaa gatttattac acaaaacaaa gtaaatacc  acttcattac tacacaaaca     360
cactacaaga aagaagttac ttcattcaaa tcaacgcatg tacataaata tataaatcat     420
gcaactactt ctagcaataa acattttact gttaaaccaa tagaagcgcc tagatataaa     480
cacccatctc aatctttaat tataaatcat catattgcag tacctggcta ccatgctcat     540
aaatttgtaa caccaggaca tgctagtatt aaaattcatc atttttgtat tgcaccaaaa     600
ataaatagtt ttaaagtaat tccatcatat ggtcacagtt cacaccgcat gcatgtacca     660
agttttcaaa gtaatacaaa atcagtacat caaaattcta gagtaaataa agtatataac     720
tataaatact tctactctta taagtagtg aaaggtgtga agaaatatta ctcattttca     780
aaatcaaatg cttataaatt tgttaaacca ccatttaata tcaaaatgt aaattaccaa     840
tatgctgctt aagtaatag ccctacacac taa                                   873

<210> SEQ ID NO 4
<211> LENGTH: 481
<212> TYPE: PRT
<213> ORGANISM: Staphylococcus aureus

<400> SEQUENCE: 4

Val Val Ser Gly Glu Glu Asn Pro Tyr Val Ser Lys Ala Ile Glu Leu
1               5                   10                  15

Lys Gly Thr Ser Asn Lys Ser Asn Thr Tyr Glu Asn Tyr Arg Glu Ser
            20                  25                  30

Leu Glu Asn Leu Ile Phe Ser Leu Ser Phe Ala Asp Tyr Glu Lys Tyr
        35                  40                  45

Glu Glu Pro Glu Tyr Asn Asn Ala Val Lys Lys Tyr Gln Gln Lys Phe
    50                  55                  60

Met Ala Glu Asp Asp Ala Leu Lys Thr Phe Leu Ser Glu Glu Lys Lys
65                  70                  75                  80

Leu Glu Lys Thr Asp Arg Ser Arg Asn Ser Asn Gly Leu Leu Gly Leu
                85                  90                  95

Thr His Glu Arg Tyr Thr Tyr Ile Phe Asp Thr Leu Lys Lys Asn Lys
            100                 105                 110

Gln Glu Phe Leu Gln Glu Ile Glu Ile Asn Leu Lys Asn Ser Asp
        115                 120                 125

Leu Lys Asp Phe Asn Asp Thr Glu Gln Tyr Asn Ala Asp Val Glu Ile
130                 135                 140

Asn Asn Leu Glu Asn Lys Val Leu Met Leu Gly Tyr Thr Phe Phe Ser
145                 150                 155                 160

Thr Tyr Lys Asp Glu Val Glu Glu Leu Tyr Ser Glu Leu Asp Leu Ile
            165                 170                 175

Val Gly Glu Val Gln Asp Lys Ser Asp Lys Lys Arg Ala Val Asn Gln
        180                 185                 190
```

```
Arg Met Leu Ser Arg Lys Lys Glu Asp Leu Glu Ser Ile Ile Asp Lys
195                 200                 205

Phe Phe Lys Glu Ile Lys Gln Glu Arg Pro Glu Asn Ile Pro Ala Leu
210                 215                 220

Thr Ser Asp Lys Asn His Asn Gln Ser Met Ala Leu Lys Leu Lys Ser
225                 230                 235                 240

Asp Thr Glu Ala Ala Lys Lys Asp Glu Ser Asn Arg Ser Ser Arg Ser
            245                 250                 255

Lys Lys Ser Leu Asp Ser Gln Asn Tyr Lys Ser Val Ser Gln Glu Val
            260                 265                 270

Thr Ala Glu Gln Lys Ala Glu Tyr Glu Lys Arg Ala Glu Glu Arg Lys
275                 280                 285

Ala Arg Phe Leu Asp Arg Gln Lys Ser Lys Lys Glu Pro Val Val Ser
290                 295                 300

Leu Glu Tyr Asp Phe Glu His Lys Gln Ser Val Asp Asn Glu Asn Asp
305                 310                 315                 320

Lys Gln Leu Val Val Ser Glu Pro Thr Lys Asn Pro Thr Leu Pro Thr
            325                 330                 335

Tyr Ile Glu Thr Thr Thr Gln Val Pro Met Pro Thr Val Glu Arg Gln
340                 345                 350

Thr Gln Gln Gln Ile Ile Tyr Lys Ala Pro Lys Gln Leu Ala Gly Leu
355                 360                 365

Asn Gly Glu Ser His Asp Phe Ser Thr Thr His Gln Thr Pro Thr Thr
370                 375                 380

Ser Asn His Thr His Asn Asn Val Val Glu Phe Glu Glu Thr Ser Ala
385                 390                 395                 400

Leu Pro Gly Arg Lys Thr Gly Ser Leu Val Gly Leu Ser Gln Ile Asp
            405                 410                 415

Ser Ser His Leu Thr Glu Arg Glu Lys Arg Val Ile Lys Arg Glu His
            420                 425                 430

Val Arg Glu Ala Gln Lys Leu Val Glu Asn Tyr Lys Asp Thr His Ser
435                 440                 445

Tyr Lys Asp Arg Leu Asn Ala Gln Gln Lys Val Asn Thr Leu Ser Glu
450                 455                 460

Gly His Gln Lys Arg Phe Asn Lys Gln Ile Asn Lys Val Tyr Asn Gly
465                 470                 475                 480

Lys

<210> SEQ ID NO 5
<211> LENGTH: 366
<212> TYPE: DNA
<213> ORGANISM: Artificial Sequence
<220> FEATURE:
<223> OTHER INFORMATION: Description of Artificial Sequence: Synthetic
      heavy chain variable region polynucleotide

<400> SEQUENCE: 5
gaagtgaagc ttgaggagtc tggaggaggc ttggtgcaac ctggaggatc catgaaactc    60
tcttgtgctg cctctggatt cactttagt gacgcctgga tggactgggt ccgccagtct   120
ccagagaagg ggcttgagtg ggttgctgaa attagaacca agctaataa tcatgcaaca   180 tactatgctg agtctgtgaa agggaggttc accatctcaa gagatgattc aaaagcagt   240 gtctacctgc aaatgaacag cttaagagct gaagacactg cattttatta ctgtaccaac   300
gtctactatg gtaacaacga tgttaaggac tactggggtc aaggaacctc agtcaccgtc   360
```

```
tcccca                                                                    366
```

<210> SEQ ID NO 6
<211> LENGTH: 124
<212> TYPE: PRT
<213> ORGANISM: Artificial Sequence
<220> FEATURE:
<223> OTHER INFORMATION: Description of Artificial Sequence: Synthetic
      heavy chain variable region polypeptide

<400> SEQUENCE: 6

Glu Val Lys Leu Glu Glu Ser Gly Gly Gly Leu Val Gln Pro Gly Gly
1               5                   10                  15

Ser Met Lys Leu Ser Cys Ala Ala Ser Gly Phe Thr Phe Ser Asp Ala
            20                  25                  30

Trp Met Asp Trp Val Arg Gln Ser Pro Glu Lys Gly Leu Glu Trp Val
        35                  40                  45

Ala Glu Ile Arg Thr Lys Ala Asn Asn His Ala Thr Tyr Tyr Ala Glu
    50                  55                  60

Ser Val Lys Gly Arg Phe Thr Ile Ser Arg Asp Asp Ser Lys Ser Ser
65                  70                  75                  80

Val Tyr Leu Gln Met Asn Ser Leu Arg Ala Glu Asp Thr Gly Ile Tyr
                85                  90                  95

Tyr Cys Thr Asn Val Tyr Tyr Gly Asn Asn Asp Val Lys Asp Tyr Trp
            100                 105                 110

Gly Gln Gly Thr Ser Val Thr Val Ser Pro Ala Ser
        115                 120

<210> SEQ ID NO 7
<211> LENGTH: 378
<212> TYPE: DNA
<213> ORGANISM: Artificial Sequence
<220> FEATURE:
<223> OTHER INFORMATION: Description of Artificial Sequence: Synthetic
      light chain variable region polynucleotide

<400> SEQUENCE: 7

```
gatattgtga tgacccagtc tcaaaaattc atgtccacat cagtaggaga cagggtcagc      60
gtcacctgca aggccagtca gaatgtggat atttatgtag cctggtatca acagaaacca     120
gggcaatctc ctaaagcact gatttactcg gcatcctacc ggttcagtgg agtccctgat     180
cgcttcacag gcagtggatc tgggacagat ttcactctca gcatcagcaa tgtgcagtct     240
gaagacttgg cagagtattt ctgtcagcaa tataacaact atccgtatac gttcggaggg     300
gggaccaagc tggaaataaa acgggctgat gctgcaccaa ctgtatccat cttcccacca     360
tccagtgaag ggcgaatt                                                   378
```

<210> SEQ ID NO 8
<211> LENGTH: 126
<212> TYPE: PRT
<213> ORGANISM: Artificial Sequence
<220> FEATURE:
<223> OTHER INFORMATION: Description of Artificial Sequence: Synthetic
      light chain variable region polypeptide

<400> SEQUENCE: 8

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Asp Ile Tyr
            20                  25                  30

-continued

```
Val Ala Trp Tyr Gln Gln Lys Pro Gly Gln Ser Pro Lys Ala Leu Ile
            35                  40                  45
Tyr Ser Ala Ser Tyr Arg Phe Ser Gly Val Pro Asp Arg Phe Thr Gly
        50                  55                  60
Ser Gly Ser Gly Thr Asp Phe Thr Leu Ser Ile Ser Asn Val Gln Ser
65                  70                  75                  80
Glu Asp Leu Ala Glu Tyr Phe Cys Gln Gln Tyr Asn Asn Tyr Pro Tyr
                85                  90                  95
Thr Phe Gly Gly Gly Thr Lys Leu Glu Ile Lys Arg Ala Asp Ala Ala
            100                 105                 110
Pro Thr Val Ser Ile Phe Pro Pro Ser Ser Glu Gly Arg Ile
        115                 120                 125

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ile Val Thr Lys Asp Tyr Ser Lys Glu Ser
1               5                   10

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      CDRL1 peptide

<400> SEQUENCE: 10

Gln Asn Val Asp Ile Tyr
1               5

<210> SEQ ID NO 11
<211> LENGTH: 3
<212> TYPE: PRT
<213> ORGANISM: Artificial Sequence
<220> FEATURE:
<223> OTHER INFORMATION: Description of Artificial Sequence: Synthetic
      CDRL2 peptide

<400> SEQUENCE: 11

Ser Ala Ser
1

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      CDRL3 peptide

<400> SEQUENCE: 12

Gln Gln Tyr Asn Asn Tyr Pro Tyr Thr
1               5

<210> SEQ ID NO 13
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      CDRH1 peptide

<400> SEQUENCE: 13

Gly Phe Thr Phe Ser Asp Ala Trp
1               5

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
      CDRH2 peptide

<400> SEQUENCE: 14

Ile Arg Thr Lys Ala Asn Asn His Ala Thr
1               5                   10

<210> SEQ ID NO 15
<211> LENGTH: 14
<212> TYPE: PRT
<213> ORGANISM: Artificial Sequence
<220> FEATURE:
<223> OTHER INFORMATION: Description of Artificial Sequence: Synthetic
      CDRH3 peptide

<400> SEQUENCE: 15

Cys Thr Asn Val Tyr Tyr Gly Asn Asn Asp Val Lys Asp Tyr
1               5                   10

<210> SEQ ID NO 16
<211> LENGTH: 102
<212> TYPE: PRT
<213> ORGANISM: Artificial Sequence
<220> FEATURE:
<223> OTHER INFORMATION: Description of Artificial Sequence: Synthetic
      humanized GMA-2105 Light chain variable region version 1
      polypeptide

<400> SEQUENCE: 16

Met Thr Gln Ser Pro Asp Ser Leu Ala Val Ser Leu Gly Glu Arg Ala
1               5                   10                  15

Thr Ile Asn Cys Lys Ala Ser Gln Asn Val Asp Ile Tyr Val Ala Trp
            20                  25                  30

Tyr Gln Gln Lys Pro Gly Gln Pro Pro Lys Ala Leu Ile Tyr Ser Ala
        35                  40                  45

Ser Tyr Arg Phe Ser Gly Val Pro Asp Arg Phe Ser Gly Ser Gly Ser
    50                  55                  60

Gly Thr Asp Phe Thr Leu Thr Ile Ser Ser Leu Gln Ala Glu Asp Val
65                  70                  75                  80

Ala Val Tyr Tyr Cys Gln Gln Tyr Asn Asn Tyr Pro Tyr Thr Phe Gly
                85                  90                  95

Gln Gly Thr Lys Val Glu
            100

<210> SEQ ID NO 17
<211> LENGTH: 102
<212> TYPE: PRT
<213> ORGANISM: Artificial Sequence
<220> FEATURE:
<223> OTHER INFORMATION: Description of Artificial Sequence: Synthetic
      humanized GMA-2105 Light chain variable region version 2
      polypeptide
```

<400> SEQUENCE: 17

Met Thr Gln Ser Pro Asp Ser Leu Ala Val Ser Leu Gly Glu Arg Ala
1               5                   10                  15

Thr Ile Asn Cys Lys Ala Ser Gln Asn Val Asp Ile Tyr Val Ala Trp
            20                  25                  30

Tyr Gln Gln Lys Pro Gly Gln Ser Pro Lys Ala Leu Ile Tyr Ser Ala
        35                  40                  45

Ser Tyr Arg Phe Ser Gly Val Pro Asp Arg Phe Ser Gly Ser Gly Ser
50                  55                  60

Gly Thr Asp Phe Thr Leu Thr Ile Ser Ser Leu Gln Ala Glu Asp Val
65                  70                  75                  80

Ala Val Tyr Tyr Cys Gln Gln Tyr Asn Asn Tyr Pro Tyr Thr Phe Gly
                85                  90                  95

Gln Gly Thr Lys Val Glu
            100

<210> SEQ ID NO 18
<211> LENGTH: 116
<212> TYPE: PRT
<213> ORGANISM: Artificial Sequence
<220> FEATURE:
<223> OTHER INFORMATION: Description of Artificial Sequence: Synthetic
      humanized GMA-2105 Heavy chain variable region version 1
      polypeptide

<400> SEQUENCE: 18

Leu Leu Glu Ser Gly Gly Gly Leu Val Gln Pro Gly Gly Ser Leu Arg
1               5                   10                  15

Leu Ser Cys Ala Ala Ser Gly Phe Thr Phe Ser Asp Ala Trp Met Asp
            20                  25                  30

Trp Val Arg Gln Ala Pro Gly Lys Gly Leu Glu Trp Val Ala Glu Ile
        35                  40                  45

Arg Thr Lys Ala Asn Asn His Ala Thr Tyr Tyr Ala Glu Ser Val Lys
50                  55                  60

Gly Arg Phe Thr Ile Ser Arg Asp Asp Ser Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Asn Val Tyr Tyr Gly Asn Asn Asp Val Lys Asp Tyr Trp Gly Gln Gly
                100                 105                 110

Thr Leu Val Thr
        115

<210> SEQ ID NO 19
<211> LENGTH: 116
<212> TYPE: PRT
<213> ORGANISM: Artificial Sequence
<220> FEATURE:
<223> OTHER INFORMATION: Description of Artificial Sequence: Synthetic
      humanized GMA-2105 Heavy chain variable region version 2
      polypeptide

<400> SEQUENCE: 19

Leu Leu Glu Ser Gly Gly Gly Leu Val Gln Pro Gly Gly Ser Leu Arg
1               5                   10                  15

Leu Ser Cys Ala Ala Ser Gly Phe Thr Phe Ser Asp Ala Trp Met Asp
            20                  25                  30

Trp Val Arg Gln Ala Pro Gly Lys Gly Leu Glu Trp Val Ala Glu Ile

```
                35                  40                  45
Arg Thr Lys Ala Asn Asn His Ala Thr Tyr Tyr Ala Glu Ser Val Lys
     50                  55                  60
Gly Arg Phe Thr Ile Ser Arg Asp Asp Ser Lys Ser Ser Val Tyr Leu
 65                  70                  75                  80
Gln Met Asn Ser Leu Arg Ala Glu Asp Thr Ala Val Tyr Tyr Cys Thr
                 85                  90                  95
Asn Val Tyr Tyr Gly Asn Asn Asp Val Lys Asp Tyr Trp Gly Gln Gly
            100                 105                 110
Thr Leu Val Thr
            115

<210> SEQ ID NO 20
<211> LENGTH: 98
<212> TYPE: PRT
<213> ORGANISM: Artificial Sequence
<220> FEATURE:
<223> OTHER INFORMATION: Description of Artificial Sequence: Synthetic
      IgG1 CH1 polypeptide

<400> SEQUENCE: 20

Ala Ser Thr Lys Gly Pro Ser Val Phe Pro Leu Ala Pro Ser Ser Lys
 1               5                  10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
         35                  40                  45
Gly Val His Thr Phe Pro Ala Val Leu Gln Ser Ser Gly Leu Tyr Ser
     50                  55                  60
Leu Ser Ser Val Val Thr Val Pro Ser Ser Ser Leu Gly Thr Gln Thr
 65                  70                  75                  80
Tyr Ile Cys Asn Val Asn His Lys Pro Ser Asn Thr Lys Val Asp Lys
                 85                  90                  95
Lys Val

<210> SEQ ID NO 21
<211> LENGTH: 15
<212> TYPE: PRT
<213> ORGANISM: Artificial Sequence
<220> FEATURE:
<223> OTHER INFORMATION: Description of Artificial Sequence: Synthetic
      IgG1 hinge region peptide

<400> SEQUENCE: 21

Glu Pro Lys Ser Cys Asp Lys Thr His Thr Cys Pro Pro Cys Pro
 1               5                  10                  15

<210> SEQ ID NO 22
<211> LENGTH: 110
<212> TYPE: PRT
<213> ORGANISM: Artificial Sequence
<220> FEATURE:
<223> OTHER INFORMATION: Description of Artificial Sequence: Synthetic
      IgG1 CH2 polypeptide

<400> SEQUENCE: 22

Ala Pro Glu Leu Leu Gly Gly Pro Ser Val Phe Leu Phe Pro Pro Lys
 1               5                  10                  15
Pro Lys Asp Thr Leu Met Ile Ser Arg Thr Pro Glu Val Thr Cys Val
            20                  25                  30
```

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
 50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 23
<211> LENGTH: 107
<212> TYPE: PRT
<213> ORGANISM: Artificial Sequence
<220> FEATURE:
<223> OTHER INFORMATION: Description of Artificial Sequence: Synthetic
      IgG1 CH3 polypeptide

<400> SEQUENCE: 23

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 24
<211> LENGTH: 107
<212> TYPE: PRT
<213> ORGANISM: Artificial Sequence
<220> FEATURE:
<223> OTHER INFORMATION: Description of Artificial Sequence: Synthetic
      IgG1 light chain constant region (kappa) polypeptide

<400> SEQUENCE: 24

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

```
<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ile Val Thr Lys Asp Tyr Ser Ala Glu Ser
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ile Val Thr Lys Asp Tyr Ser Lys Ala Ser
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ile Val Thr Lys Asp Tyr Ser Ala Ala Ser
1               5                   10
```

ANTIBODY SPECIFIC TO STAPHYLOCOCCUS AUREUS, THERAPEUTIC METHOD AND DETECTION METHOD USING SAME

RELATED APPLICATIONS

The present patent document is a continuation application of U.S. patent application Ser. No. 15/583,384 filed May 1, 2017, issued as U.S. Pat. No. 10,023,655, and which is a continuation of U.S. patent application Ser. No. 15/155,209 filed May 16, 2016, issued as U.S. Pat. No. 9,637,555, which is a divisional application of U.S. patent application Ser. No. 14/604,521 filed Jan. 23, 2015, issued as U.S. Pat. No. 9,353,189 which claims the benefit of the filing date under 35 U.S.C. § 119(e) of Provisional U.S. Patent Application Ser. No. 61/931,236, filed Jan. 24, 2014, each of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Jan. 21, 2015, is named 163-303_SL.txt and is 29,860 bytes in size.

BACKGROUND

Infections caused by *Staphylococcus aureus* ("*S. aureus*") are a major causative agent of hospital and non-hospital infections. These infections cause longer hospitalization time and cost. *S. aureus* infections range from common, minor skin infections to blood-borne infections of the heart valves called infective endocarditis.

Infective endocarditis may be used as a model for illustrating *S. aureus* infection. Endocarditis is an inflammation of the endocardium, the inner layer of the heart. In some variations, it involves the heart valves. In other variations it may involve the interventricular septum, the chordae tendineae, the mural endocardium, and even surfaces of implanted medical devices such as intracardiac devices and prosthetic valves.

One characteristic of endocarditis is a lesion, which may also be referred to as a vegetation. A vegetation includes but is not limited to, a mass of platelets, fibrin, microcolonies of microorganisms, and inflammatory cells. In some variations, infective endocarditis vegetations may also include a center of granulomatus tissue, e.g., a collection of the immune cells called macrophages. Granulomatus tissue may fibrose (e.g., form excess tissue) and/or calcify.

Heart valves do not receive dedicated blood supply, which may blunt the immune response, making it difficult for immune defenses (such as white blood cells) to directly reach the valves via the bloodstream. Valves may have an increased susceptibility to infection, e.g. bacterial infection, due to (among other factors) the blunted immune response. The lack of blood supply to the valves may also decrease the effectiveness of traditional treatments, since drugs (e.g., those delivered via bloodstream) also have difficulty reaching infected valves.

*S. aureus* infection rates continue to increase. *S. aureus* acute infective endocarditis is 25-47% fatal despite antibiotic therapy. Vancomycin is a common antimicrobial treatment for infections caused by *S. aureus* (e.g., methicillin resistant *S. aureus*). Of great concern is the observation that drug resistant strains of *S. aureus* are rapidly evolving. The rapid spread of hypervirulent, multi-drug resistant strains of *S. aureus* suggest *S. aureus* will likely become resistant to all antibiotics and an even greater threat to public health. This threat is exacerbated due to, among other things, the reluctance of drug companies to develop new antibiotics.

BRIEF SUMMARY

We provide monoclonal antibodies able to recognize and bind to staphylocoagulase. The monoclonal antibodies are able to bind to and interfere with, modulate, and/or inhibit the binding interactions between the staphylocoagulase protein and its ligand protein prothrombin in blood and tisdues. It is effective in inhibiting the activation of prothrombin.

The provided monoclonal antibodies are represented by sequences SEQ ID NO.: 5, SEQ ID NO.: 6, SEQ ID NO.: 7, SEQ ID NO.: 8. The CDRs are represented by SEQ ID NOS.: 10-15. A cell line expressing monoclonal antibodies specific to staphylocoagulase and homologs thereof is deposited with the ATCC under accession number PTA-120537.

Other systems, methods, features, and advantages of the disclosure will be, or will become, apparent to one with skill in the art upon examination of the following figures and detailed description. It is intended that all such additional systems, methods, features and advantages be included within this description, be within the scope of the invention, and be protected by the following claims.

BRIEF DESCRIPTION OF THE DRAWINGS

The following description of the drawings and the various system, method, and apparatus is not intended to limit the inventive system, methods and apparatus disclosed herein to one embodiment, but rather to enable any person skilled in the art of art of antibody production to make and use the inventive system, method and monoclonal antibodies.

FIG. 13 is a chart comparing amino acid substitutions in three mutated peptides (SEQ ID NOS 25-27, respectively, in order of appearance).

FIG. 30 shows comparison of binding characteristics of murine GMA-2105 and chimeric GMA-2105.

DETAILED DESCRIPTION

Figure 1:
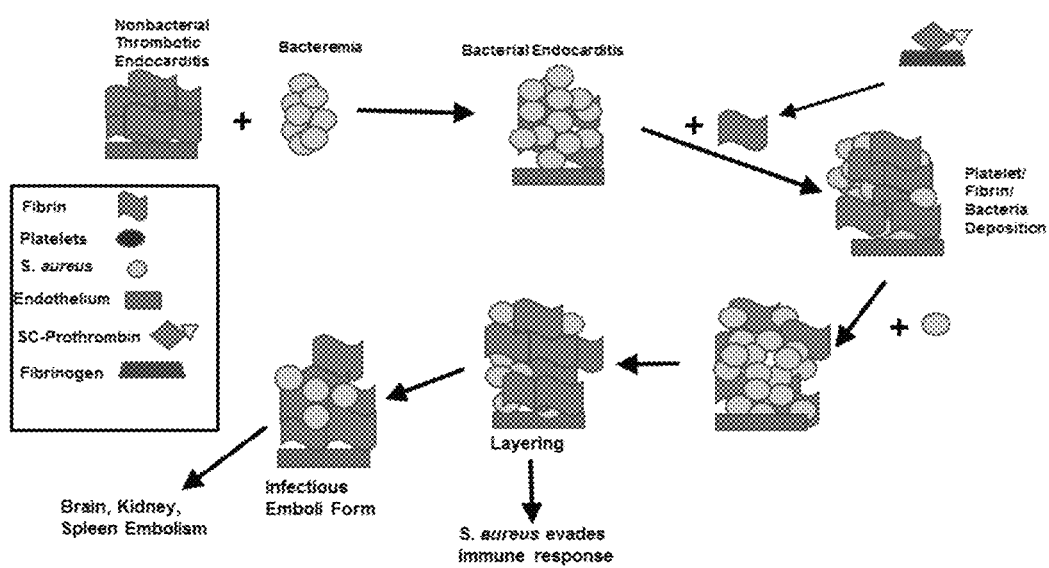
FIG. 1 provides a schematic of the pathogenesis of acute bacterial endocarditis.

*S. aureus*, is a highly adaptive human pathogen, causing recurrent skin and soft tissue infections by evading the immune system. *S. aureus* colonizes the nose and skin of 20-30% of the human population. Healthy individuals with intact skin and mucosal barriers may harbor *S. aureus* with no adverse result. However, when the integrity of the skin and mucosa are breached, *S. aureus* can invade and enter the tissue and blood stream and potentially cause injury.

Pathologies associated with *S. aureus* colonization include but are not limited to meningitis, sepsis, pneumonia. Pathologies also include endocarditis and septic arthritis in high risk populations, such as infants, immunocompromised adults, and intravenous drug users. The presence of foreign materials in the body, including intravenous catheters, greatly increases the risk of developing *S. aureus*-induced endocarditis. For example, catheters may become coated with fibrinogen and fibronectin, to which the bacterium can easily adhere.

Therapy of staphylococcus infections, including but not limited to, MRSA infections, is complicated by the fact that the organisms have evolved resistance to commonly used therapeutics and quickly develop immunity to new therapeutics. For example, despite antibiotic therapy, MRSA infections are associated with a poor outcome. It is estimated that only 5% of *S. aureus* isolates are susceptible to penicillin treatment. Another feature of staphylococcal infections is its reoccurrence rate. Further complication treatment indications, clinical and experimental observations suggest that infections with *S. aureus* do not generate protective immune response.

The immune invasion strategies of *S. aureus* allow it to survive in the blood. Through the blood and/or subepidermal tissues, *S. aureus* encounters and escapes the host innate immune defenses. *S. aureus* displays cell-surface proteins and secreted virulence factors, including the procoagulant staphylocoagulase (SC) which allow it to compromise the effectiveness of both the innate and adaptive immune responses. Some examples of how *S. aureus* evades the host immune system includes, but is not limited to, invading endothelial cells and neutrophils, inhibiting the complement system, and subverting the coagulation system for infective purposes.

Acute infective endocarditis (AIE) is one of the illnesses caused by *S. aureus*. Other illnesses include etastatic infections migrating to bones/joints, spleen, kidneys, liver, and lungs; sepsis; toxic shock syndrome; and pneumonia (among others). *S. aureus* recruits new virulence factors and antibiotic resistenace encoded by mobile genetic elements (MGEs) from other strains or different bacterial species. The emergence of methicillin-resistant *S. aureus* (MRSA) is attributed to MGE transfer, as is the ongoing global epidemic of the hypervirulent USA300 strain of community associated-MRSA (CA-MRSA).

Antibiotic resistance of CA-MRSA is leading to a reliance on vancomycin for treatment of severe infections. However, *S. aureus* has also developed resistance to this antibiotic. Partially vancomycin-resistant *S. aureus* with thickened cell walls have been described and clinical isolates carrying the vanA gene complex have appeared in the United States.

The adaptability of *S. aureus* and the rapid spread of hypervirulent and multidrug-resistant strains supports the prediction that *S. aureus* will soon become resistant to all available antibiotics. This huge public health problem will be associated with increased morbidity and mortality based on the propensity of *S. aureus* to cause many potentially lethal infections. The elderly are particularly susceptible and as the U.S. population ages there will be an increase in these infections.

The public health problem is exacerbated by the lack of interest of pharmaceutical companies in developing new antibiotics. This derives from the rapid emergence of antibiotic resistance that reduces the market life of the drugs and low profit due to the short treatment time. Attempts to create staphylococcal vaccines have uniformly failed, as demonstrated by clinical trial data.

To begin to address the public health threat posed by *S. aureus* we disclose new monoclonal antibodies as mechanism-targeted inhibitors of *S. aureus* procoagulant staphylocoagulase (SC).

Accute infectious endocarditis (AIE) pathogenesis of *S. aureus* has at least two initiating events (FIG. 1). First, injury to the endothelium covering the heart valves. In one example, injury may result from turbulent flow due to a congenital or acquired defect. Injury may also result from the presence of intravascular catheters, intravenous drug use, or physiological stress from hypersensitivity states, hormonal changes, or exposure to high altitude.

Injury may initiate coagulation and formation of a sterile thrombus composed of, e.g., fibrin and platelets. Coagulation may be initiated due to exposure of blood to, among others, tissue factor. Exposure of blood to tissue factor triggers activation of blood coagulation. Activation of blood coagulation may result in formation of a sterile thrombus. The sterile thrombus may be composed of, among other factors, activated platelets and fibrin (e.g., thrombin-generated fibrin).

A compromised system may permit bacteria to enter the bloodstream and adhere to the sterile thrombis, for example, by binding fibrinogen and fibronectin. *S. aureus* is among the most common bacterial pathogens. *S. aureus* expresses cell surface components, for example but not limited to adhesins. *S. aureus* cell surface components include but are not limited to wall-bound adhesins that bind fibrin(ogen), e.g., clumping factor A (ClfA) and other microbial surface components. The various cell surface components recognize adhesive matrix molecules that mediate binding of the bacteria to the site of vascular injury.

The most aggressive *S. aureus* strains in AIE secrete SC and also vWFbp, which bind to host prothrombin, abbreviated "Il." The active (active is designated "*") SC●prothrombin*(SC●Il*) and vWFbp●Il* complexes bind host fibrinogen as their substrate and convert it into fibrin. Deposition of fibrin propagates the formation of platelet-fibrin-bacteria vegetations, characteristic of AIE, at the site of vascular injury.

Vegetations grow by layering of more bacteria onto fibrin, and fibrin generation by the SC●Il* and vWFbp●Il* catalytic complexes (FIG. 1). Fibrin layers on vegetations and protects the bacteria from clearance by immune cells and killing by antibiotics. Turbulent flow nearby vegetations propagates endothelial damage across heart valves, ultimately leading to valvular dysfunction due to tissue damage and heart failure. Large vegetations produce infectious emboli that spread through the bloodstream to distant sites where they form abscesses in the brain, spleen, and kidneys.

Embolism to the brain is common in *S. aureus* AIE occurring in 30% of patients and results in ischemic or hemorrhagic stroke, which is often fatal. Mortality from AIE is very high at 25-47%, despite aggressive antibiotic treatment. Clearly, adjunctive therapy is sorely needed, which we begin to address here in the form of mechanism-based monoclonal antibodies.

Figure 2:
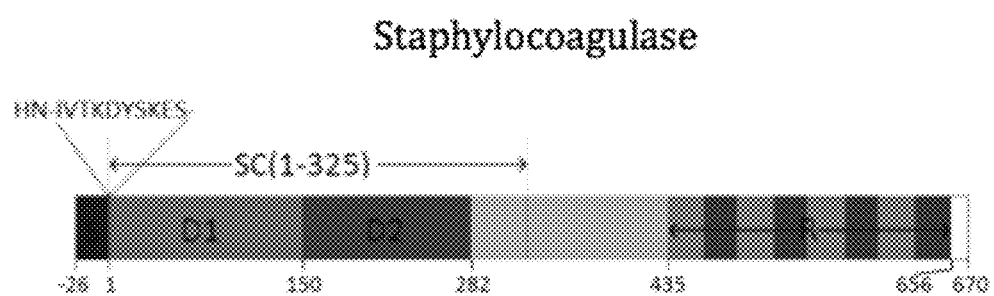
FIG. 2 provides an exemplary representation of staphylocoagulase, and discloses SEQ ID NO: 9.
Figure 3:
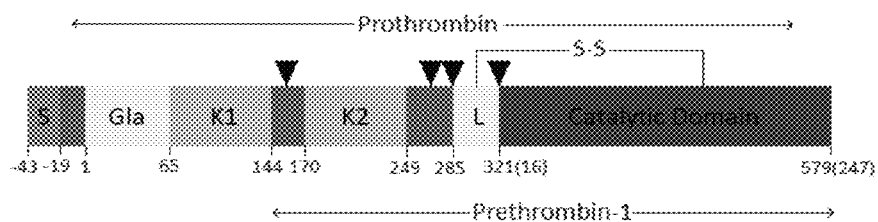
FIG. 3 provides an exemplary representation of prothrombin.
Figure 4:
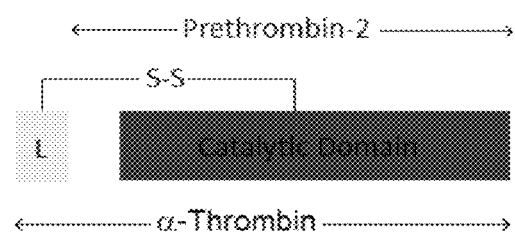
FIG. 4 provides an exemplary representation of thrombin.
Figure 5:
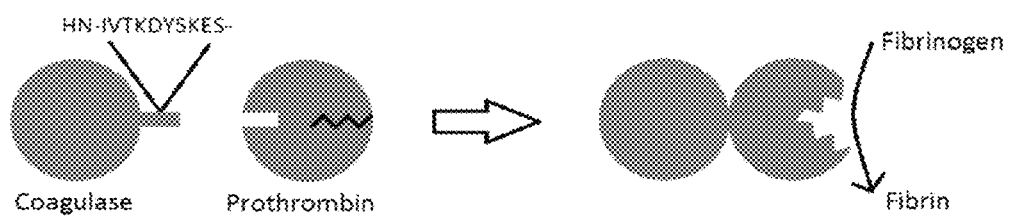
FIG. 5 provides a representation of staphylocoagulase and prothrombin and their interaction resulting in the non-proteolytic formation of an active site and discloses SEQ ID NO: 9.

FIG. 2 provides a schematic diagram of staphylocoagulase. FIG. 3 provides a schematic diagram of prothrombin. FIG. 5 is a diagram of the interaction of staphylocoagulase with prothrombin resulting in the non-proteolytic formation of an active site. The N-terminal Ile of staphylocoagulase forms a salt bridge with Asp 194 (chymostrypsin numbering) in the prothrombin activation site resulting in a conformational change in prothrombin which nonproteolytically stabilizes the thrombin active site. Fibrinogen can then be cleaved to fibrin by thrombin, resulting in the formation of a clot. (FIG. 1).

The SC(1-325)●Pre 2* structure shows the N-terminus of SC ($Ile^1$-$Val^2$) inserted into the $Ile^{16}$ (chymotrypsinogen numbering) N-terminal binding cleft of the prothrombin fragment designated Pre 2 where it forms a salt-bridge with $Asp^{194}$ that triggers non-proteolytic activation of Pre 2 within the complex.

Recognizing the problems inherent in existing treatments, such as but not limited to, rapid resistance including emerging Vancomycin resistance and off-target events associated with anticoagulants, we disclose a method, system, and monoclonal antibody secreting cell line which enables the treatment of S. aureus infection in a specific and accurate manner by using SC-specific monoclonal antibodies.

Accordingly, we provide monoclonal antibodies that can bind to the staphylocoagulase protein from *S. aureus*, or certain subregions thereof, with high affinity, preventing the staphylocoagulase protein from forming an active prothrombin-bacterial cofactor complex. The monoclonal antibodies disclosed herein, thereby prevent the formation of fibrin, which prevents *S. aureus*' ability to create the vegetations used to protect the bacteria from clearance by immune cells and killing by antibiotics.

We demonstrate herein the effectiveness of anti-staphylocoagulase monoclonal antibodies to prevent fibrin formation (as demonstrated by clotting data, among other things) and to successfully treat *S. aureus* infections in an animal model.

The results of our experiments herein were surprising in light of the fact that the role of staphylocoagulase as a virulence factor in *S. aureus* infection has been in doubt due to conflicting results in a rat model of endocarditis that showed no role of staphylocoagulase, whereas a role for staphylocoagulase was demonstrated in a blood-borne pneumonia mouse model.

Fully developed *S. aureus* abscesses exhibit a defined structure with the bacteria in the center, bordered by fibrin-rich barriers that protect the bacteria from immune cells and antibiotics. The role of staphylocoagulase has been in doubt also in light of research demonstrating that *S. aureus* lacking the staphylocoagulas gene could form abscesses.

The use of anticoagulants, which have the potential to produce lethal bleeding, to treat AIE has been debated. Given the complexity of thrombin regulation through its two exosites that bind protein substrates, inhibitors, and regulatory macromolecules, and its many procoagulant and anticoagulant roles, systemic inhibition of thrombin (via anti-coagulants) in an attempt to inhibit staphylocoagulase /vWFbp-Il* may lead to off-target events with adverse consequences. Comparison of 35 patients with *S. aureus* AIE to those with native valve AIE, of which none were taking anticoagulants, to 21 with prosthetic valve AIE 90% of which were taking anticoagulants, found that the groups had similar incidence of neurologic embolisms, and the mortality in the anticoagulant group was 71% compared to 37% in the no anticoagulant group. More of those patients had brain hemorrhages. An old study found the opposite outcome for a small group of patients with prosthetic valves; i.e., mortality was slightly greater (57% vs. 47%) if anticoagulant therapy was stopped.

Our novel monoclonal antibody targeting staphylocoagulase avoids the off-target events experienced with anticoagulants. The SC monoclonal antibody inhibits fibrin formation by targeting the staphylocoagulase protein specifically. It therefore has a localized effect at the site of *S. aureus* infections and does not have system-wide consequences.

The mouse models for blood coagulation are similar to the human coagulation system. Emeis, et al., A guide to murine coagulation factor structure, function, assays and genetic alterations, J. Thromb. Haemost. 2007; 5:670-9, incorporated herein by reference in its entirety. Numerous therapeutics directed at human coagulation systems (clotting, platelets, fibrinolysis) are similarly effective at comparable doses in mice. This suggests that targeting staphylocoagulase with an antibody might give physiologic and pharmacologic data that is reflective of what happens in humans.

Targeting *S. aureus* via the host hemostatic response is a novel therapeutic approach to treating *S. aureus* infection. The mechanistic details of prothrombin activation are well known. (See, e.g., Krishnaswamy, S., The transition of prothrombin to thrombin, J. Thromb. Haemost, 2013; 11:256-76, incorporated herein by reference in its entirety.) The novel approach involves using a monoclonal antibody to block *S. aureus*' ability to form a fibrin mesh, preventing the course of disease. (The course of disease is illustrated in FIG. 1). A therapeutic monoclonal antibody provides advantages over vaccines. In contrast to a vaccine that requires the development of an immune response which may take several days or months, the therapeutic monoclonal antibody can be used in acute infections and can also offer prophylactic protection before an infection. We demonstrate that our novel anti-staphylocoagulase monoclonal antibodies prevent fibrin formation.

Accordingly, we provide monoclonal antibodies that can bind to the SC protein from *S. aureus*, or certain subregions thereof, with high affinity and which can thus be useful in methods to treat, prevent, or diagnose staphylococcal infections.

We also provide a therapeutic antigen binding protein which recognizes an epitope of the SC protein from *S. aureus* that contains residues 1-10 from the N-terminal SC ("SC(1-10)").

We also provide a therapeutic antigen binding protein which recognizes an epitope of the SC protein from *S. aureus* that contains residues 1-3, 1-4, 1-5, 1-6, 1-7, 1-8, 1-9, or 1-10 of the SC protein.

In a variation, the therapeutic antigen binding protein is an antibody or antigen binding fragment and/or derivative thereof.

We also provide monoclonal antibodies which are able to bind SC and peptides which are generated from the SC or a subregion thereof and which are useful in methods to treat, prevent, or diagnose staphylococcal infections. In one example, we provide monoclonal antibodies generated from the N-terminal SC, in another example, we provide monoclonal antibodies generated from SC(1-10). In another example, we provide monoclonal antibodies generated from a peptide comprising amino acids IVTKDYSKES (SEQ ID No. 9) and homologs and/or degenerations thereof.

We also provide monoclonal antibodies to the SC protein which can be useful in inhibiting the SC-II activation.

We also provide monoclonal antibodies able to recognize and bind to Staphylocoagulase protein (SEQ ID No. 2) and other proteins presenting sequences homologous to Staphylocoagulase including vWFbp (SEQ ID No. 4), and other bacteria possessing Staphylocoagulase or sequences homologous to this protein.

We also provide monoclonal antibodies to recognize and bind to proteins encoded by staphylocoagulase nucleotide sequences (SEQ ID No. 1) and other proteins encoded by sequences homologous to staphylocoagulase. The monoclonal antibodies may also recognize and bind to proteins of bacteria possessing staphylocoagulase or sequences homologous to staphylocoagulase.

We also provide monoclonal antibodies able to recognize and bind to peptide sequence IVTKDYSKES-CONH2 (SEQ ID NO: 9), Staphylocoagulase peptide sequence IVTKDYSKES-CONH2 (SEQ ID NO: 9), and other proteins presenting sequences homologous to peptide sequence IVTKDYSKES-CONH2 (SEQ ID NO: 9), and Staphylocoagulase peptide sequence IVTKDYSKES-CONH2 (SEQ ID NO: 9).

We also provide a method which enables the treatment of *S. aureus* in a specific and accurate manner by using SC specific monoclonal antibodies generated using SC(1-10) peptide sequence (SEQ ID No. 9 and amino acids 1-10 of Seq. ID. NO. 2).

We provide an antibody specifically binding to a polypeptide comprising a SC, wherein the monoclonal antibody was generated using a peptide comprising the amino acid sequence IVTKDYSKES (SEQ ID No. 9).

We also provide an antibody capable of binding SC(1-10) and inhibiting the binding of SC to prothrombin.

We also provide an antibody capable of binding SC(1-10) (SEQ ID No. 9) inhibiting the activation of prothrombin$^{3Q}$ (a non-cleavable form of prothrombin) by SC(1-246) with 0.9 nM affinity.

An antibody capable of binding to SC which has an affinity constant ($K_D$) for SC of between 0.1 nm and 10 nM, specifically 2 nM for binding of 1.6 mol Bodipy-SC/mol mAb.

We provide a hybridoma cell line producing a monoclonal antibody capable of binding SC, in which said hybridoma cell line has accession number ATCC PTA-120537.

We also provide a method of treating an animal infected with *S. aureus* by injecting the infected animal with monoclonal antibody against SC.

We also provide a therapeutic antigen binding protein, such as an antibody or antigen binding fragment and/or derivative thereof, which binds *S. aureus* SC and which comprises the heavy chain variable region amino acid sequence of SEQ ID NO 6 and the antibody light chain variable region of SEQ ID NO 8.

We also provide an antigen binding protein, such as an antibody or antigen binding fragment thereof which specifically binds to SC protein and comprises a heavy chain region that is a variant of the sequences set forth in SEQ ID NO 6.

We also provide an antigen binding protein, such as an antibody or antigen binding fragment thereof which specifically binds to SC protein and comprises a light chain region that is a variant of the sequence set forth in SEQ ID NO 8.

We also provide a therapeutic antigen binding protein, such as an antibody or antigen binding fragment and/or derivative thereof, which binds SC and which comprises the following CDRs:

```
CDRL1:    QNVDIY (residues 27-32 of SEQ ID No. 8 and
          SEQ ID No: 10)

CDRL2:    SAS (residues 50-52 of SEQ ID No. 8 and
          SEQ ID No.: 11)

CDRL3:    QQYNNYPYT (residues 89-97 of SEQ ID No. 8
          and SEQ ID No: 12)

CDRH1:    GFTFSDAW (residues 26-33 of SEQ ID No. 6
          and SEQ ID NO: 13)

CDRH2:    IRTKANNHAT (residues 51-60 of SEQ ID No. 6
          and SEQ ID NO: 14)

CDRH3:    CTNVYYGNNDVKDY (residues 98-111 of SEQ ID
          No. 6 and SEQ ID NO: 15).
```

We also provide an antigen binding protein, such as an antibody or antigen binding fragment thereof which specifically binds SC and comprises CDR's which are variants of the sequences set forth in SEQ ID NOS.: 10-15.

A variant includes a partial alteration of the CDR, heavy chain and/or light chain amino acid sequence by deletion or substitution of one to several amino acids of the CDR, heavy chain and/or light chain, or by addition or insertion of one to several amino acids to the CDR, heavy chain, and/or light chain, or by a combination thereof. The variant may contain 1, 2, 3, 4, 5, or 6 amino acid substitutions, additions or deletions in the amino acid sequence of the CDR, heavy chain, and/or light chain sequence. The substitutions in amino acid residues may be conservative substitutions, for example, substituting one hydrophobic amino acid for an alternative hydrophobic amino acid.

Antigen binding proteins which are variants of the CDR, heavy chain, and/or light chain will have the same or similar functional properties to those comprising the CDR, heavy chain, and/or light chain described herein. Therefore, antigen binding proteins which comprise a variant CDR will bind to the same target protein or epitope with the same or similar binding affinity to the CDR, heavy chain, and/or light chain described herein.

An exemplary antibody is GMA-2105 murine monoclonal antibody. In a variation there is provided a humanized or chimeric antibody comprising the following CDRs of GMA-2105:

```
CDRL1:    QNVDIY (residues 27-32 of SEQ ID No. 8 and
          SEQ ID No: 10)

CDRL2:    SAS (residues 50-52 of SEQ ID No. 8 and
          SEQ ID No.: 11)

CDRL3:    QQYNNYPYT (residues 89-97 of SEQ ID No. 8
          and SEQ ID No: 12)

CDRH1:    GFTFSDAW (residues 26-33 of SEQ ID No. 6
          and SEQ ID NO: 13)

CDRH2:    IRTKANNHAT (residues 51-60 of SEQ ID No. 6
          and SEQ ID NO: 14)

CDRH3:    CTNVYYGNNDVKDY (residues 98-111 of SEQ ID
          No. 6 and SEQ ID NO: 15).
```

For example, a chimeric antibody may comprise the variable regions of the GMA-2105 antibody, namely SEQ ID No: 6 ($V_H$) and SEQ ID No. 8 ($V_L$). A first example of a humanized antibody based on GMA-2105 is an antibody comprising a heavy chain having SEQ ID NO.: 18. A second example of a humanized antibody based on GMA-2105 is an antibody comprising a heavy chain sequence having SEQ ID NO. 19. A third example of a humanized antibody based on GMA-2105 is an antibody comprising a light chain having SEQ ID No. 16. A fourth example of a humanized antibody based on GMA-2105 is an antibody comprising a light chain having SEQ ID No. 17. A fifth example of a humanized antibody based on GMA-2105 is an antibody comprising a heavy chain sequence having either SEQ ID NO. 18 or SEQ ID No.: 19 and a light chain sequence having either SEQ ID NO. 16 or SEQ ID No.: 17.

Method of Generating Monoclonal Antibodies to Staphylocoagulase

We provide monoclonal antibodies that can recognize and bind to, among other proteins, staphylocoagulase, and homologs thereof. In one method, the antibodies are raised against a synthetic peptide comprising the sequence IVTKDYSKES (SEQ ID No.: 9). The synthetic peptide was used to generate a panel of murine monoclonal antibodies. Monoclonal antibodies recognizing staphylocoagulase may be raised from peptides comprising expressed and purified staphylocoagulase, and/or synthetic peptides raised from other subregions or larger immunogenic regions of the staphylocoagulase protein.

Antibodies may be obtained in conventional ways including steps of introducing the staphylocoagulase antigen, subregions, peptides, or degenerate versions thereof, into a host animal, followed by isolation of the antibody-producing spleen cells and formation of a suitable hybridoma.

An inhibitory mouse anti-staphylocoagulase antibody designated GMA-2105 was produced against a peptide IVTKDYSKES (SEQ ID No.: 9), representing residues 1-10 of staphylocoagulase (SEQ ID No.: 2), with the achieved goal of blocking activation of prothrombin by binding to the staphylocoagulase sequence that inserts into prothrombin.

Example Method of Generating Anti-Staphylocoagulase Monoclonal Antibody

Female Balb/c mice approximately 6-8 weeks old received an initial intraperitoneal (ip) injection of 100 μg staphylocoagulase peptide (sequence IVTKDYSKES, SEQ ID NO 9) conjugated with-keyhole limpet hemocyanin (KLH) and emulsified in complete Freund's adjuvant on day 0. Booster injections of 50 μg of the above peptide conjugate emulsified in incomplete Freund's were given on days 10, 20 and 30.

Two additional 50 μg injections (peptide-KLH conjugate in incomplete Freunds adjuvant) were given on days 61 and 111. A serum sample from each mouse was collected on Day 122 and the antibody titer measured by solid-phase Enzyme Linked Immunosorbant Assay (ELISA) using the staphylocoagulase peptide SC(1-10) (SEQ ID No.: 9) conjugated to ovalbumin coated on 96-well ELISA plates at 2 ug/ml. Uncoated areas of the wells were blocked with albumin from bovine serum (BSA). The wells were then incubated with dilutions of the mouse serum to test whether the serum contained antibodies to the staphylocoagulase peptide SC(1-10) (SEQ ID. No.: 9). Bound antibodies were detected with anti-mouse IgG secondary antibody conjugated to horseradish peroxidase. The plates were then incubated with o-phenylenediamine (OPD) substrate which undergoes a color change in the presence of HRP the intensity of which can be measured using absorption at 490 nm wavelength in a microplate reader.

Figure 6:
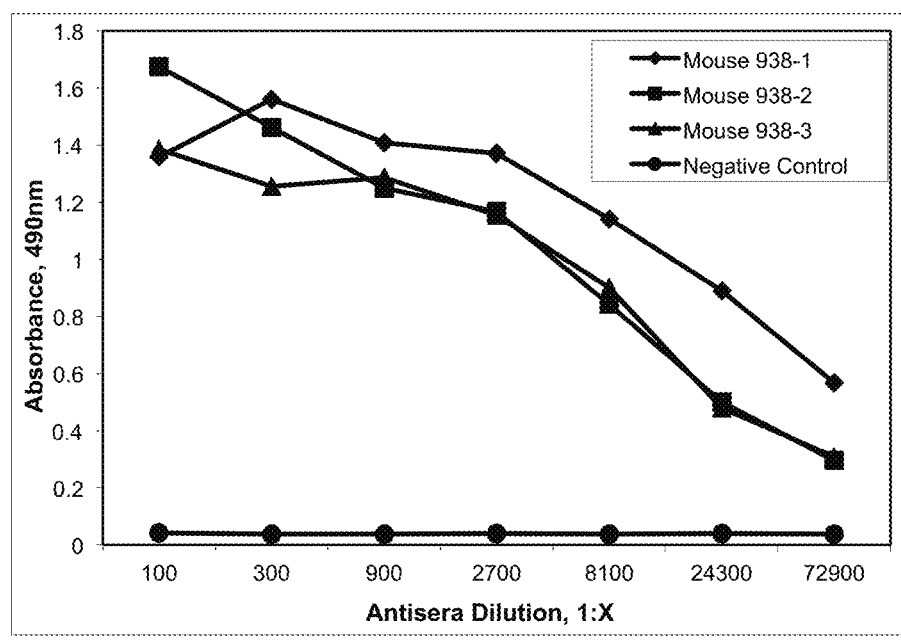
FIG. 6 shows immune response of three mice injected with IVTKDYSKES (SEQ ID NO: 9) conjugated to carrier protein.

FIG. 6 provides the results of the ELISA demonstrating the presence of anti-staphylocoagulase antibodies in mouse serum of mice (designated 938-1, 938-2, and 938-3 on FIG. 6) injected with the staphylocoagulase peptide SC(1-10)

(SEQ ID No.: 9). Serum from an irrelevant mouse was used as a negative control (designated Negative Control on FIG. 6).

Fusions were performed using three of the mice resulting in positive clones. Splenocytes from the mouse designated 938-3 on FIG. 6 were harvested for a fusion on Day 128. A total of $2.9 \times 10^8$ spleen cells were mixed with $3 \times 10^7$ NS1 myeloma cells, centrifuged to pellet the cells. The supernatant was aspirated and 1.0 ml 50% polyethylene glycol in media (PEG) was added drop wise over 1 minute to allow cell membranes to fuse. Culture media was then added drop wise to dilute the PEG 20-fold. The fused cells were centrifuged and resuspended in 100 ml Selection media consisting of Dulbecco's Modified Eagle Medium high glucose (DMEM) base with added 15% fetal bovine serum (FBS), 100 uM hypoxanthine, 2% (v/v) Hybridoma Cloning Supplement (Roche), 4 mM L-glutamine, 50 U/ml penicillin, 50 µg/ml streptomycin, 1× nonessential amino acids and the selective agent azaserine at 5.7 uM used to kill unfused NS1 cells. The cell suspension was dispensed into 24 well plates, 1 ml/well. Plates were incubated at 37° C. in 8% $CO_2$ atmosphere for 6 days and then fed with 1 ml per well of Growth media consisting of the components described above minus the azaserine. Cells were allowed to grow an additional 4-5 days.

On Day 11 post fusion, cell supernatants were tested for the presence of anti-staphylocoagulase peptide antibodies by ELISA using the ELISA assay described above. The positive well was subcloned by the limiting dilution method in Growth media to obtain a monoclonal cell line.

For this method cells were seeded into 96-well plates at sufficiently low density to increase the probability of a colony growing from a single cell. Approximately 10 days later, wells were screened by solid-phase ELISA to identify antibody-producing clones. The contents of the positive well was subcloned again by limiting dilution seeding into a single 96 well plate. The contents of the positive well was given the designation 2A1.5H4.B7. The cells were grown to sufficient numbers for cryopreservation and antibody production.

For antibody production, cells were grown to high density in roller bottles in 500 ml serum-free media. Antibody was purified from the supernatant by allowing the antibody to bind to protein G Sepharose on an affinity column (Pierce) that allows non-antibody proteins to flow through. Bound antibodies were then eluted from the Sepharose using 0.1 M glycine, pH 2.7. Eluted antibodies were neutralized to pH 7 with 1 M Tris buffer. A buffer transfer into phosphate buffered saline (PBS) was performed by dialysis using 30 kd molecular weight cut off dialysis tubing. Purified antibody was stored at 4° C. in the presence of 0.1% sodium azide as a preservative.

Figure 10:
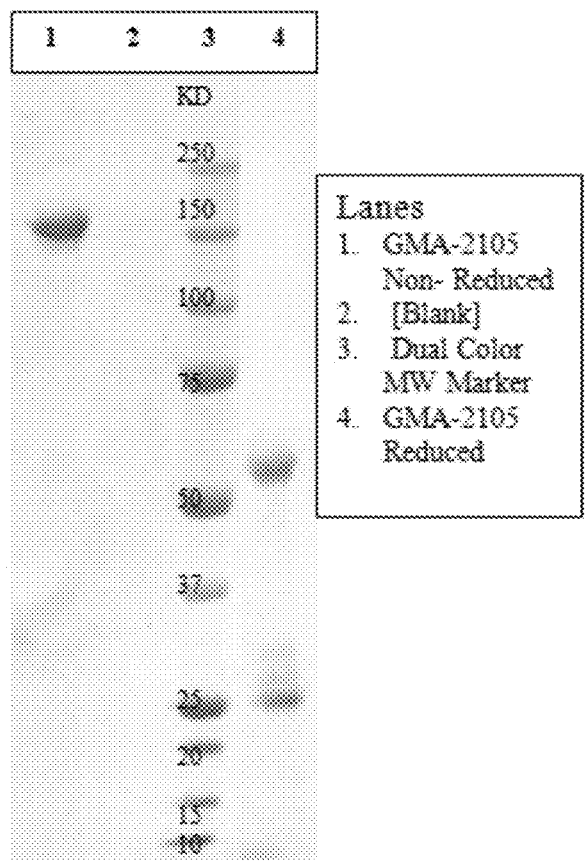
FIG. 10 shows the purified GMA-2105 antibody IgG on the SDS-PAGE assay according to a variation.

FIG. 10 is an SDS-PAGE image of purified GMA-2105. An antibody sample of 3 µg was electrophoresed at 200V on a 4-12% Bis-Tris gel under reducing and non-reducing conditions. Lane 1 shows GMA-2105 under non-reduced conditions resulting in a single band of molecular weight 155 kDa. Lane 4 shows GMA-2105 under reduced conditions with about 55 kDa (heavy chain) and 26 kDa (light chain). Lane 3 refers to the molecular weight marker. Lane 2 is empty.

Figure 7:
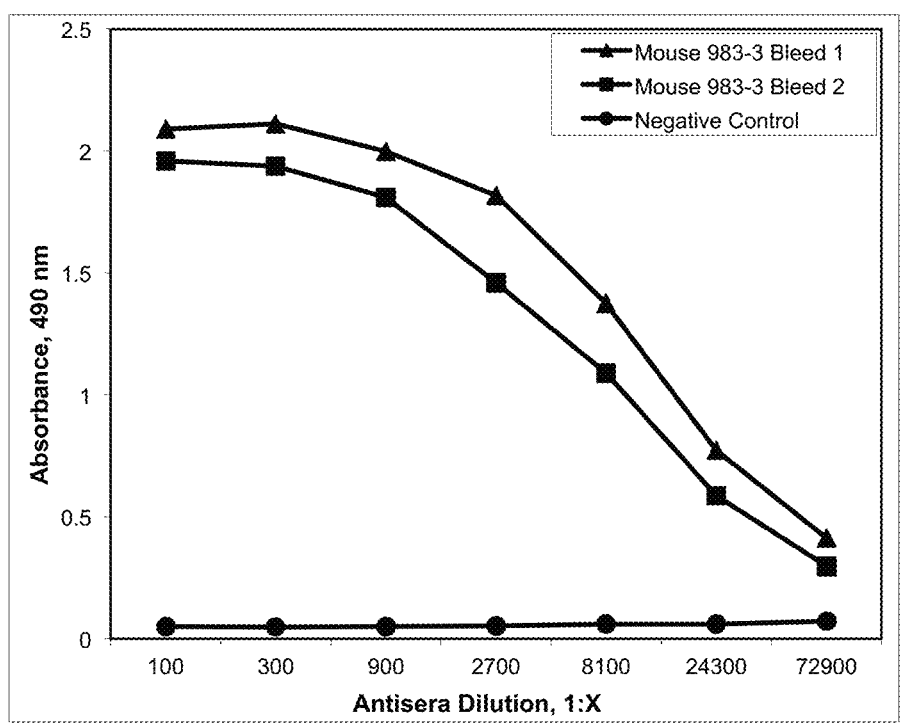
FIG. 7 shows serum immune response from splenocyte donor mouse used for hybridoma production.

FIG. 7 shows the serum immune response from the splenocyte donor mouse that was used for hybridoma production. The splenocyte donor mouse was bled at two time points. Binding of mouse serum antibody to staphylocoagulase peptide SC(1-10) (SEQ ID No.: 9) ovalbumin coated wells of a 96 well plate was detected using a goat anti-mouse secondary antibody conjugated to horseradish peroxidase. Substrate ortho-phenylenediamine conversion to product was measured at 490 nm using a spectrophotometer. The negative control was the serum from an irrelevant mouse.

Figure 8:
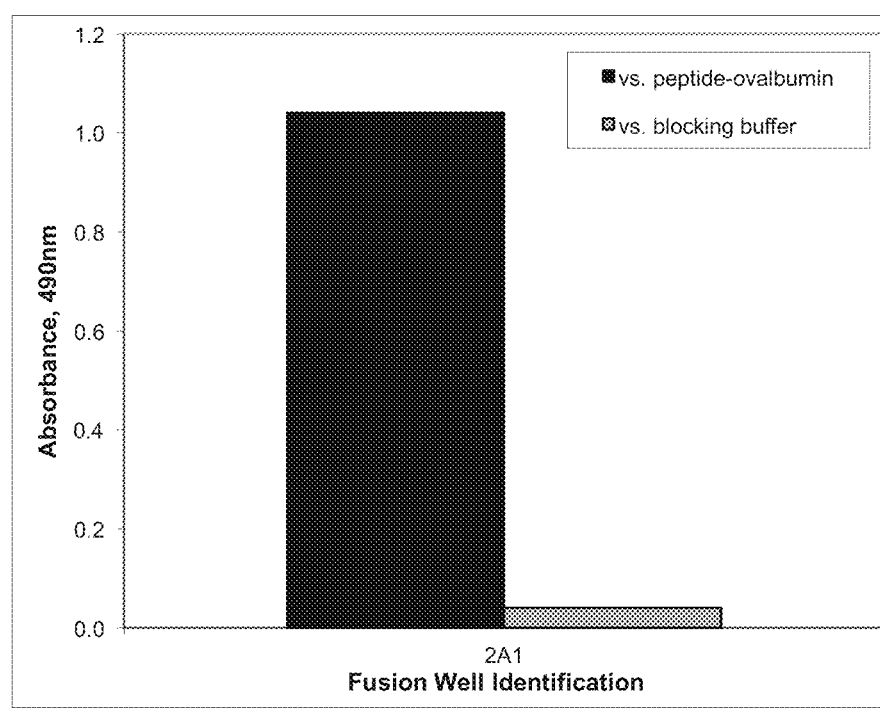
FIG. 8 shows binding of anti-IVTKDYSKES (SEQ ID NO: 9) antibody in hybridoma cell supernatant in ELISA.

FIG. 8 shows the binding of anti-staphylocoagulase antibody GMA-2105 in hybridoma cell supernatant to SC(1-10) peptide ovalbumin conjugate bound to the wells of a 96 well plate. The antibody-antigen complex was detected using a goat anti-mouse secondary antibody conjugated to horseradish peroxidase. Substrate ortho-phenylenediamine conversion to product was measured at 490 nm using a spectrophotometer. The negative control was a well that was coated with carbonate buffer with no antigen and then blocked with blocking buffer. The negative control well did not contain the peptide conjugate.

Figure 9:
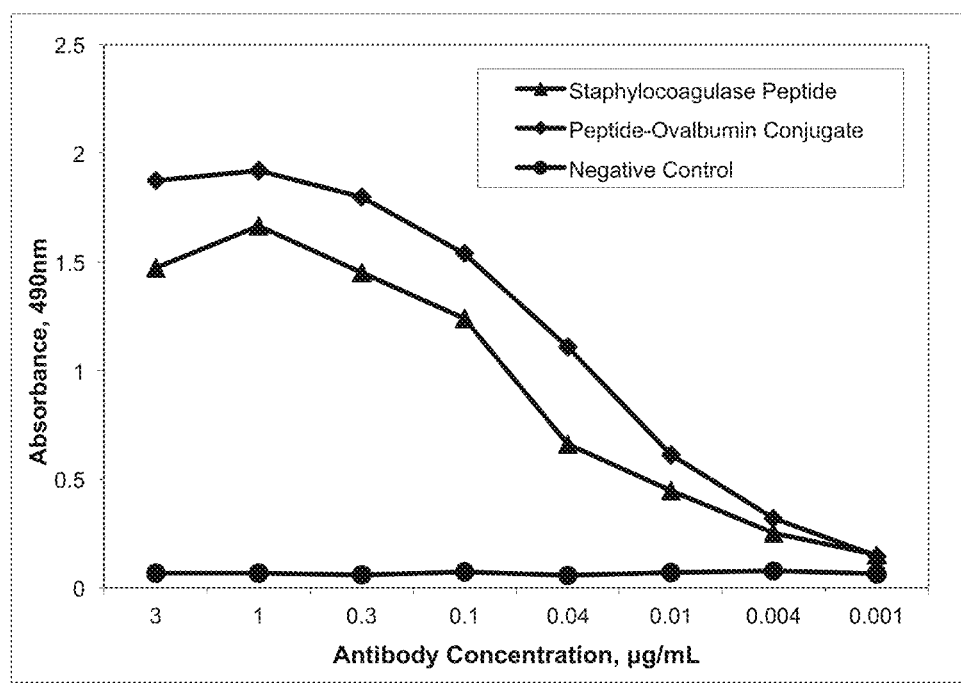
FIG. 9 shows purified antibody designated GMA-2105 binding to conjugated- and unconjugated-IVTKDYSKES (SEQ ID NO: 9) in ELISA.

FIG. 9 demonstrates the ability of the purified monoclonal antibody GMA-2105 disclosed herein to bind to the staphylocoagulase peptide SC(1-10) (residues 1-10 of SEQ ID No.: 2). For ease of reference, the purified antibody was designated GMA-2105. The curve shows binding of GMA-2105 to unconjugated staphylocoagulase peptide SC(1-10)(SEQ ID NO.:9), and staphylocoagulase peptide SC(1-10)(SEQ ID NO.:9) -ovalbumin conjugate. A purified, irrelevant mouse IgG was used as a negative control.

Figure 11:
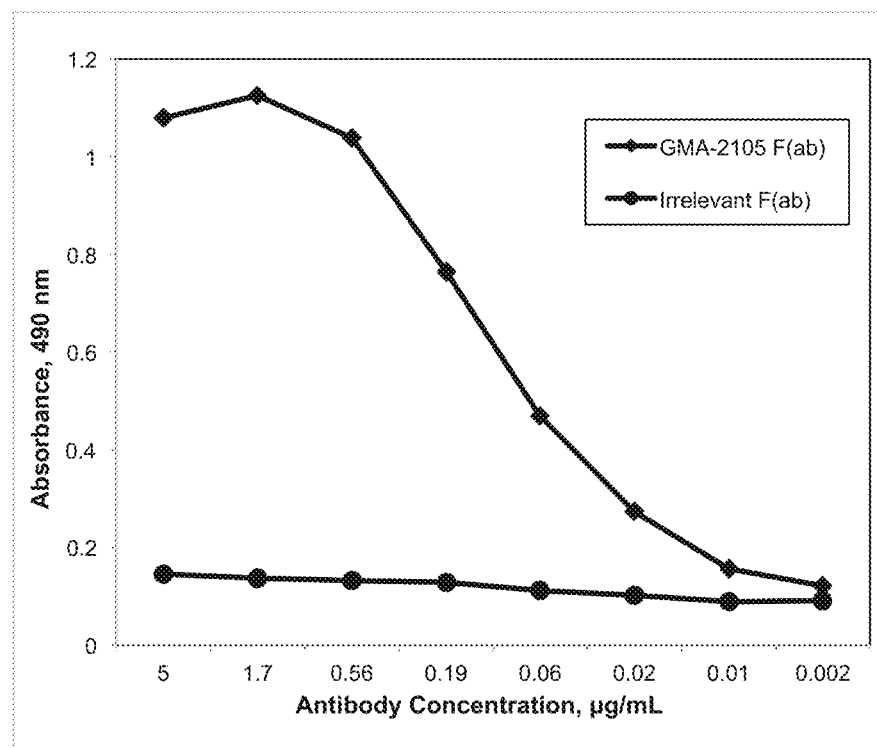
FIG. 11 shows binding of GMA-2105 F(ab) to IVT-KDYSKES (SEQ ID NO: 9) coated wells in ELISA.

FIG. 11 demonstrates the successful binding of GMA-2105 fragment antigen-binding fragment (F(ab) fragment). The GMA-2105 F(ab) was tested by ELISA against the IVTKDYSKES peptide (SEQ. ID. No.: 9). The negative control was a purified irrelevant F(ab) fragment. This demonstrates that the GMA-2105 F(ab) fragment, alone, is capable of binding staphylocoagulase IVTKDYSKES peptide (SEQ ID No.: 9).

Figure 12:
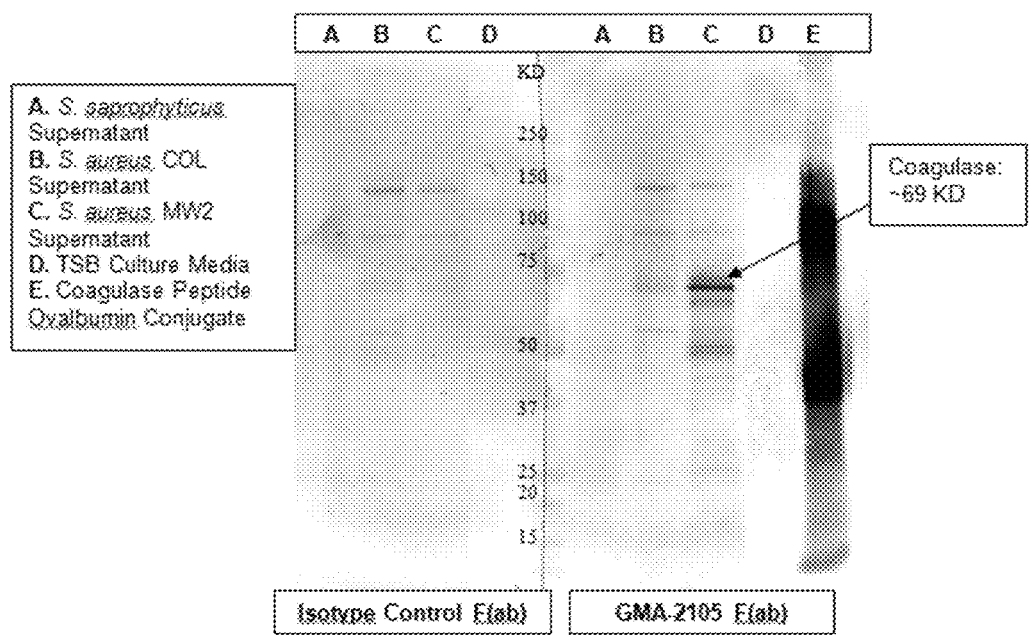
FIG. 12 shows a Western blot detection of staphylocoagulase in cultured bacteria of various strains using purified GMA-2105 F(ab) fragments.

FIG. 12 shows a Western blot detection of staphylocoagulase in cultured bacteria of various strains using purified GMA-2105 F(ab) fragments. Lanes A, B, and C contain concentrated (10×) supernatants from identically cultured bacteria. Lane A: *S. saprophyticus* (coagulase negative bacterium control); Lane B: *S. aureus* strain COL (MRSA); Lane C: *S. aureus* strain MW2 (MRSA); Lane D: media blank; Lane E: staphylocoagulase peptide conjugated to ovalubumin (SEQ ID No.: 9). The Western blot demonstrated the ability of the GMA-2105 F(ab) fragments to bind staphylocoagulase, even in cultured bacteria.

Experiment: Demonstration of GMA-2105 Binding to Staphylocoagulase Variants

There are reported strain specific sequence differences at residue positions 8 and 9 of staphylocoagulase (SEQ ID. No.: 2). For example, various strains have been found to have amino acid substitutions at positions 8 and/or 9. *Wantabe*, et al., Genetic Diversity of Staphylocoagulase Genes (coa): Insight into the evolution of variable chromosomal virulence factors in Staphylococcus aureus. PLoS ONE 2009; 4(5): 1-11, incorporated herein by reference in its entirety. To demonstrate the ability of GMA-2105 to recognize and bind to variations of staphylocoagulase among different *S. aureus* strains, we synthesized three peptides with alanine substitutions at positions 8 of SEQ ID No. 9 ("Mutated Peptide Ala 8"), position 9 of SEQ ID No. 9 ("Mutated Peptide Ala 9"), and position 8 and 9 of SEQ ID No.: 9 ("Mutated Peptide Ala 8 & 9") (see FIG. 13). We measured the binding of each synthetic peptide (Mutated Peptide Ala 8, Mutated Peptide Ala 9, and Mutated Peptide Ala 8 & 9) to GMA-2105 in solution.

Figure 14:
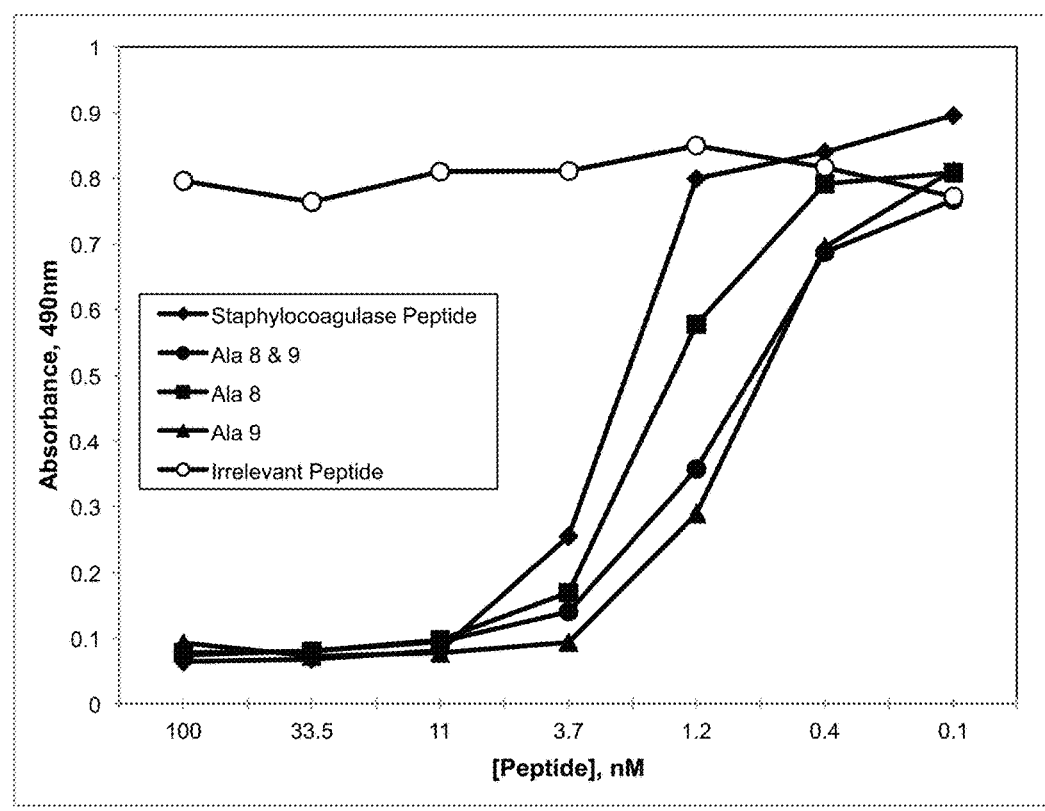
FIG. 14 shows binding of GMA-2105 to variant staphylocoagulase peptides to in solid phase competitive inhibition ELISA.
Figure 15:
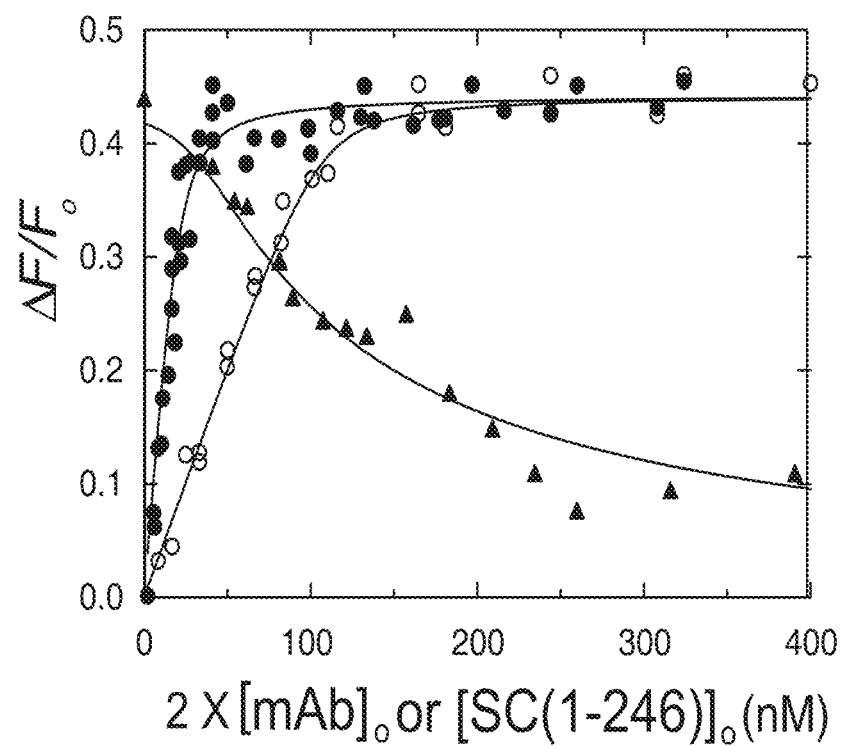
FIG. 15 shows BOPIDY-labeled staphylocoagulase fragment SC(1-325) with (S7C) titrated with GMA-2105 in solution in the presence of unlabeled SC(1-246).
Figure 16:
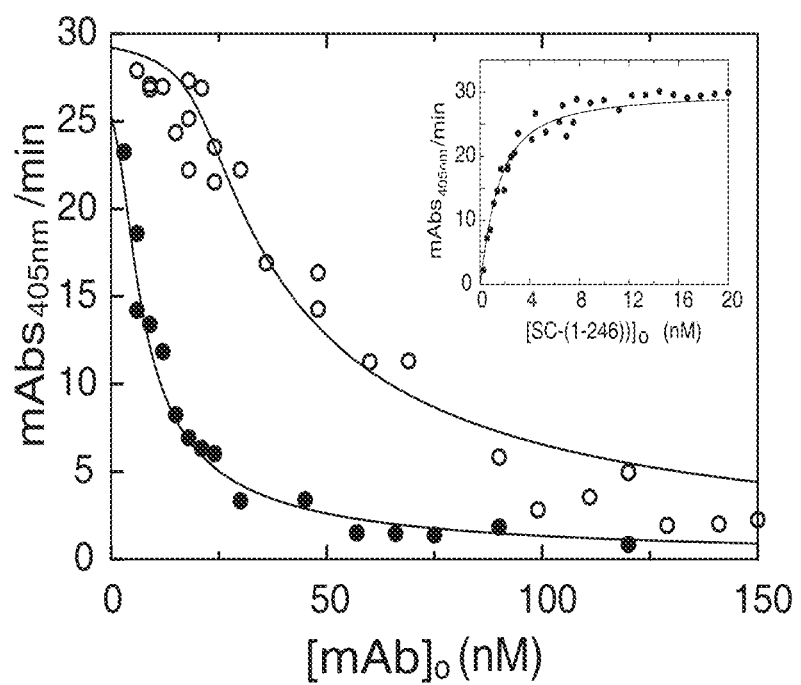
FIG. 16 shows inhibition of SC(1-246)-ProT$^{3Q}$ by GMA-2105.
Figure 17:
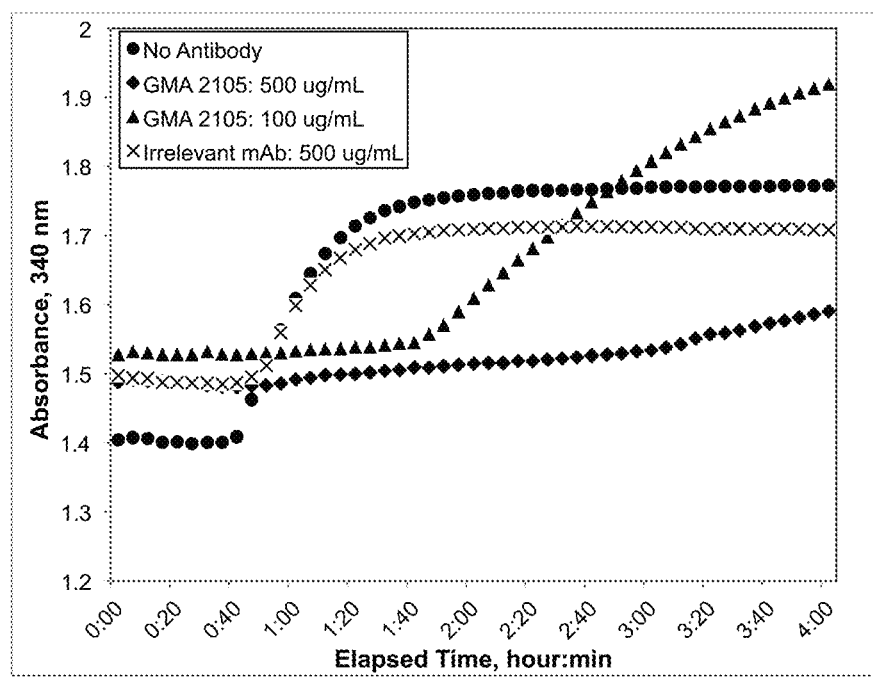
FIG. 17 shows results of clotting assay demonstrating that GMA-2105 blocks staphylocoagulase activity inhibiting prothrombin activation and downstream plasma clotting.
Figure 18:
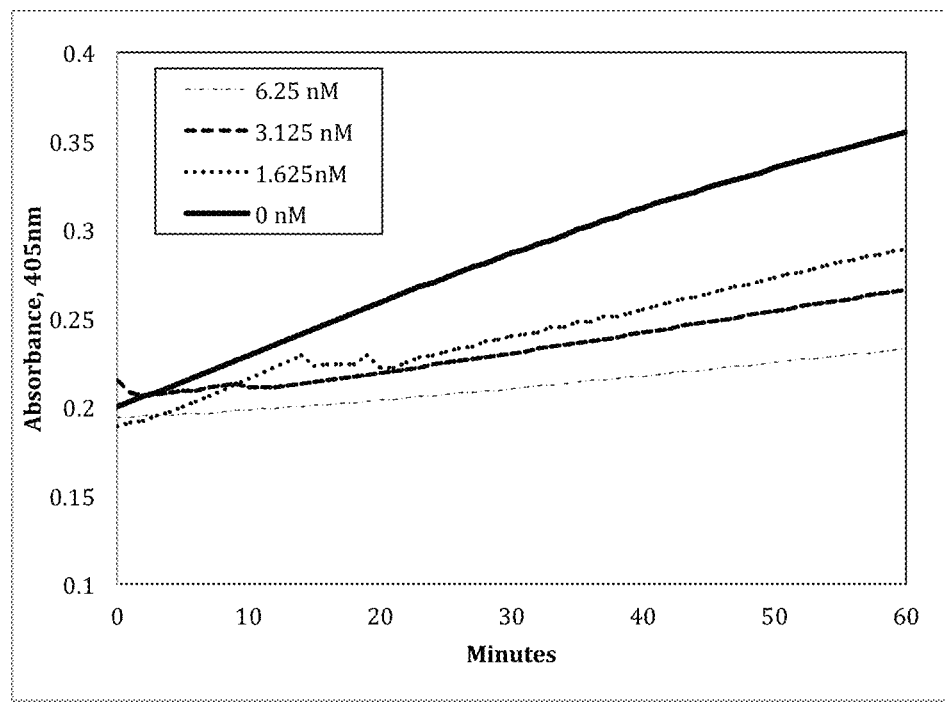
FIG. 18 shows the effect of GMA-2105 on prothrombin activation by staphylocoagulase activity in *S. aureus* supernatant.

FIG. 14 shows the results of the competitive binding assay. We tested binding of Mutated Peptide Ala 8, Mutated Peptide Ala 9, and Mutated Peptide Ala 8 & 9 to GMA-2105 in a solid phase competitive inhibition assay. GMA-2105 was incubated with increasing concentrations of each of Mutated Peptide Ala 8, Mutated Peptide Ala 9, and Mutated Peptide Ala 8 & 9 (referred to hereafter as "GMA-2105—Mutated Peptide samples") in solution overnight at 4 degrees C. The incubation was followed by transfer of the GMA-2105—Mutated Peptide samples to wells coated with the non-mutated peptide, IVTKDYSKES (SEQ ID. No.:9) and blocked with 0.1% BSA PBS. After a 30 minute incubation, wells were washed with PBS containing 0.05% TWEEN 20, followed by addition of goat anti-mouse secondary antibody conjugated to horseradish peroxidase. Substrate ortho-phenylenediamine conversion to product was measured at 490 nm using a spectrophotometer. The negative control as was a purified irrelevant synthetic peptide.

Mutated Peptide Ala 8, Mutated Peptide Ala 9, and Mutated Peptide Ala 8 & 9, all bound antibody in solution. As shown in FIG. 14. Mutated Peptide Ala 8, Mutated Peptide Ala 9, and Mutated Peptide Ala 8 & 9 each and all inhibited binding of antibody onto wells coated with IVTKDYSKES (SEQ ID No.: 9) in competitive assay.

As demonstrated in the example, we provide an isolated monoclonal antibody, and/or a purified monoclonal antibody (e.g., purified from ATCC PTA-120537). The antibody may be used in, for example, methods of inhibiting activation of prothrombin, for example but not limited to, inhibiting the binding of SC and/or vWFbp to prothrombin. In additional to the methods described above, monoclonal antibodies may be produced using a variety of methods, e.g., methods found in *Monoclonal Antibodies: Methods and Protocols,* ISBN: 1588295672; *Antibodies: A Laboratory Manual,* ISBN: 0879693142, incorporated herein by reference in their entirety.

Resulting antibodies may be prepared in a number of forms, including chimeric, humanized, or human in addition to murine. Monoclonal antibodies may be prepared from a single chain, such as the light or heavy chains. Alternatively or additionally, monoclonal antibodies may be prepared from active fragments, e.g., fragments that retain the binding characteristics (e.g., specificity and/or affinity) of the whole antibody. Antisera prepared using monoclonal or polyclonal antibodies provided herein may be prepared in a number of suitable ways.

EXAMPLE

Inhibition of Prothrombin Activation

A high affinity monoclonal antibody GMA-2105 targeting the staphylocoagulas N-terminus residues inhibits prothrombin activation. In solution, the antibody bound Ser 7 to Cys mutant of SC(1-325). Binding studies were done using the BODIPY-labeled staphylocoagulase SC (S7C)(1-325) (SEQ ID No.: 2, positions 1-325 with Cys at position 7). The change of fluorescence upon antibody binding is measured as a function of the unlabeled ligand concentration and fitting the data to the quadratic binding equation gives the dissociation constant ($K_D$), and the stoichiometry (n). *Panizzi,* et al., Fibrinogen substrate recognition by staphylocoagulase-(pro)thrombin complexes, J. Biol. Chem. 2006; 281:118-95.

Analysis of the increase in BODIPY fluorescence on GMA-2105 binding gave $K_{ID}$ 2 nM for binding of 1.6 mol BODIPY-SC/mol GMA-2105, indicating that the antibody GMA-2105 is bivalent and binds the staphylocoagulase SC(1-246)(positions 1-246 of SEQ ID No.: 2) with high affinity. Binding of the labeled staphylocoagulase SC(1-246) (positions 1-246 of SEQ ID No.: 2) to the GMA-2105 was competitively inhibited by binding of an unlabeled staphylocoagulase peptide representing positions 1-246 (SC(1-246)) of SEQ ID No.: 2, with $K_D$ 4 nM (descending curve in FIG. 15), indicating comparable affinity of the antibody for staphylocoagulase (positions 1-246 of SEQ ID No.: 2).

FIG. 15 shows equilibrium binding of GMA-2105 to staphylocoagulase SC(1-246) (positions 1-246 of SEQ ID No.: 2). The results indicate high-affinity interaction. Direct binding of BODIPY-SC(S7C) at 27nM (●) and 130 nM (○) probe titrated with GMA-2105 caused fluorescence increase, whereas unlabeled SC(1-246) (triangles) displaced BODIPY-SC(S7C) labeled staphylocoagulase from binding the antibody. Simultaneous fit of all datasets provide the Kd for the unmodified competitor to the antibody.

The GMA-2105 antibody inhibits prothrombin$^{3Q}$ activation by SC(1-246) (positions 1-246 of SEQ ID No. 246) with 0.9 nM affinity (FIG. 16). Inhibition of prothrombin activation is complete as determined by analysis of inhibition at two SC(1-246) (positions 1-246 of SEQ ID No. 246) concentrations as competitive binding of prothrombin$^{3Q}$ and GMA-2015 to SC(1-246) (positions 1-246 of SEQ ID No. 246), meaning that staphylocoagulase bound to the GMA-2105 cannot activate prothrombin.

Using fluorescently labeled staphylocoagulase (SC(1-325) and Ser to Cys at position 7 of SEQ ID No. 2), and unlabeled GMA-2105, gave a KD of 0.99±0.07 nM and a stoichiometry of 2 mol staphylocoagulase/mol GMA-2105. Concentrations were: BODIPY-staphylocoagulase (1-325) at 27 nM ( ) and 130 nM (○) titrated with GMA-2105 and unlabeled staphylocoagulase (1-246)(residues 1-246 of SEQ ID No. 2).

FIG. 16 shows inhibition of SC(1-246)●prothrombin$^{3Q}$ by GMA-2105. This data gave identical $K_D$ and n for antibody binding to staphylocoagulase. Rates of S2238 hydrolysis by prothrombin (1 nm) and SC(1-246) at 5.6 nM(●) and 28 nM (○) versus GMA-2105 concentration. The inset shows titration of 1nM prothrombin with SC(1-246).

Example

Inhibition of Plasma Clotting

GMA-2105 inhibits *S. aureus* plasma clotting. FIG. 17 shows the inhibition of plasma clotting by increasing concentration of purified GMA-2105. GMA-2105 at varying concentrations was incubated with supernatant from *S. aureus* strain Tager 104 grown to OD 600 of 0.5 for one hour at room temperature followed by addition of an equal volume of rabbit plasma. Clotting was measured using a microplate spectrophotometer at 340 nm. Addition of GMA-2105 at 100 ug/mL (triangles) and 500 ug/mL (diamonds) prevented clotting as shown. The controls included an isotype matched antibody (XX) and no antibody (solid circle).

FIG. 18 demonstrates the effect of increasing concentrations of GMA-2105 to inhibit staphylocoagulase activity in *S. aureus* Tager supernatant. *S. aureus* Tager supernatant was incubated with or without GMA-2105 antibody at various concentrations (6.25 nM GMA-2105, 3.125 nM GMA-2105, 1.625 nM GMA-2105, 0 nM GMA-2105) for three hours at room temperature in a buffer of 50 nM HEPES pH 7.4, 150 nM NaCl, 5 mM $CaCl_2$, 1 mg/mL PEG8000. Prothrombin was added to a 40 nM final concentration. The samples were incubated for three hours at room temperature. After incubation, S-2238 chromogenic substrate was added to a final concentration of 286 uM and the resulting absorbance was read at 405 nM for 1 hour.

Example

GMA-2105 Antibody Does Not Aggregate

Figure 19:
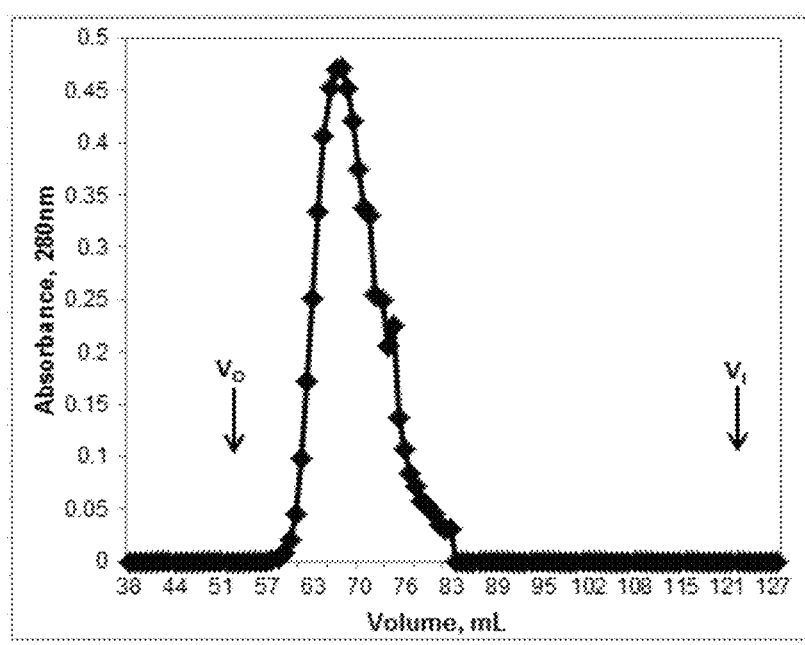
FIG. 19 shows purified GMA-2105 analyzed by size exclusion chromatography.
Figure 20:
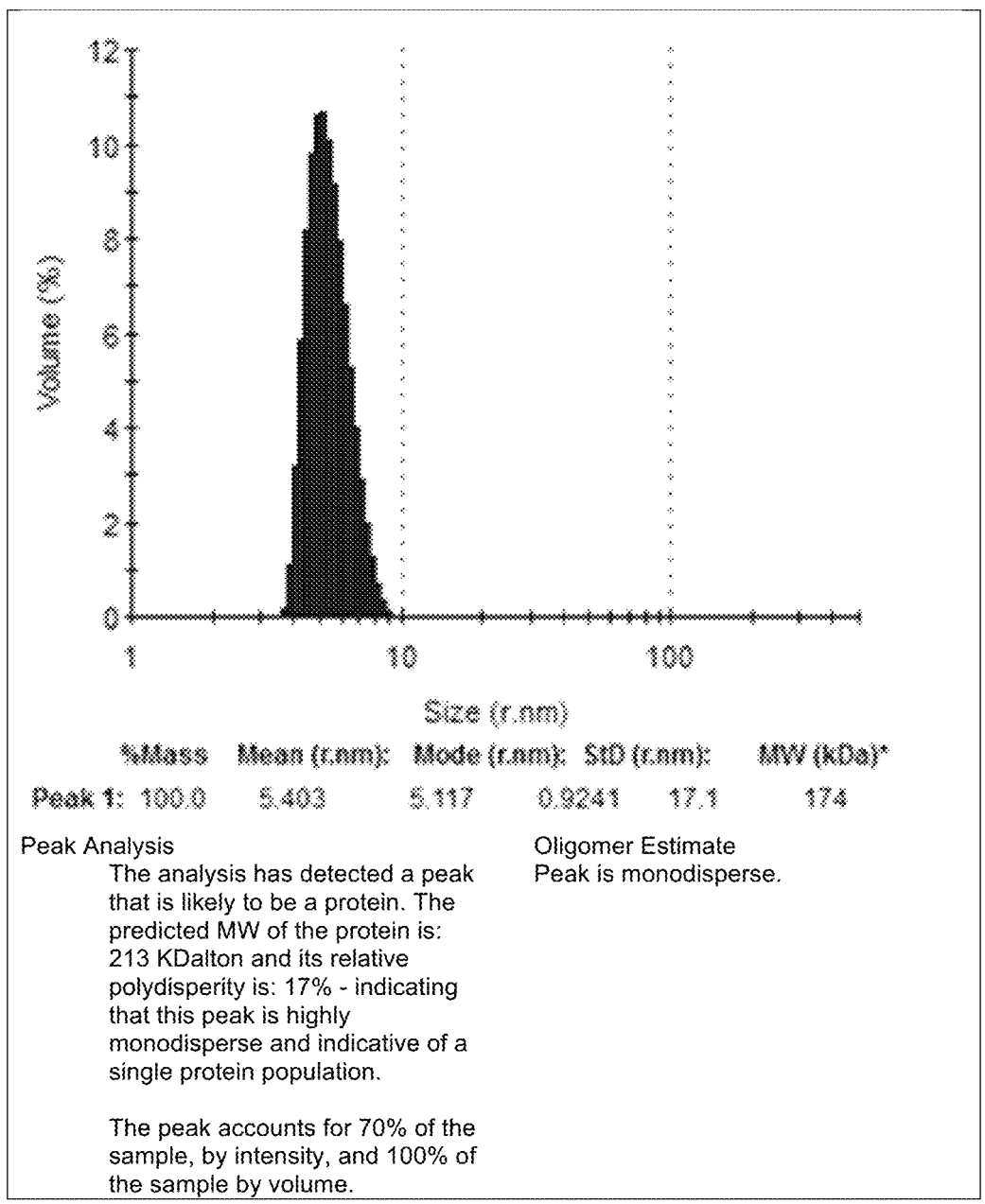
FIG. 20 shows dynamic light scattering of purified GMA-2105.

Protein therapeutics, including monoclonal antibodies, have the potential for instability in which the physical state of the protein changes even through the chemical composition is unaltered. Several clinical trials with monoclonal antibodies have failed due to antibody aggregation. Two methods are commonly used to measure protein aggregation: size exclusion chromatography and light scattering. FIGS. 19 and 20 demonstrate evidence using these methods that isolated GMA-2105 does not aggregate.

FIG. 19. Purified GMA-2105 was analyzed by size exclusion chromatography using a column packed with SEPHACRYL 300 resin. A total of 4.2 mgs or 5.9 absorbance units were loaded onto the column in a volume of 1.5 mL. Fractions (1 mL) were collected and absorbance determined by spectrophotometry at 280 nM. Recovery off the column was 5.6 absorbance units, accounting for 96 percent of the sample that was loaded.

FIG. 20. Dynamic light scattering using MALVERN ZETASIZER NANO S at 25.0 degrees Celsius. A 1 mL fraction from the size exclusion chromatography analysis was filtered using a WHATMAN 0.2 uM filter, loaded into a disposable sizing cuvette and run using protein analysis software. GMA-2105 appears to be adequately stabilized in solution following production and purification.

Example

Survival Study and Pharmacokinetics

The mAb targeting SC(1-10) characterized in Preliminary Results promotes survival in a mouse model of *S. aureus* sepsis. Injection of purified antibody into mice followed by challenge with *S. aureus* gave the survival curve shown in FIG. 22. The experiment shows statistically significant survival over the controls (irrelevant antibody or phosphate-buffered saline).

Figure 21:
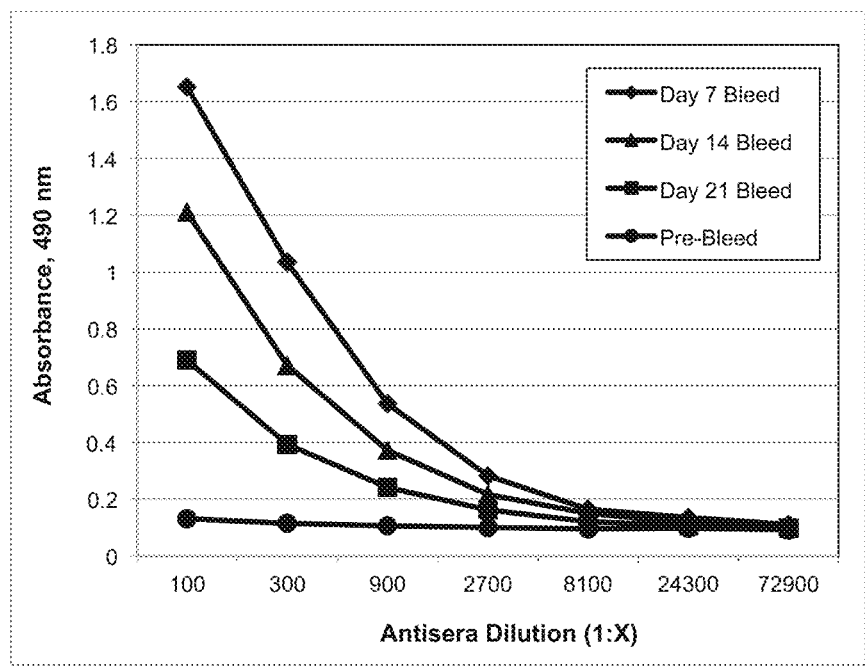
FIG. 21 shows detection of GMA-2105 antibody in the blood of mice 21 days post intraperitaneal administration.

FIG. 21. Detection of GMA-2105 antibody in the blood of mice 21 day post administration. C57BL/6 mice were injected intraperitioneal with 120 μg of the mAb against SC(1-10) (GMA-2105). Every 7 days for a total of 21 days, blood was collected from the tail vein of each of the three mice. The antisera was diluted and added to a 96 well ELISA plate coated with the peptide IVTKDYSKES (SEQ ID. No.: 9) and blocked with 0.1% BSA/PBS. After a 1 hour incubation, wells were washed with PBS containing 0.05% TWEEN 20 followed by addition of goat anti-mouse secondary antibody conjugated to horseradish peroxidase. Substrate orth-phenylenediamine conversion to product was measured at 490 nm using a spectrophotometer.

Figure 22:
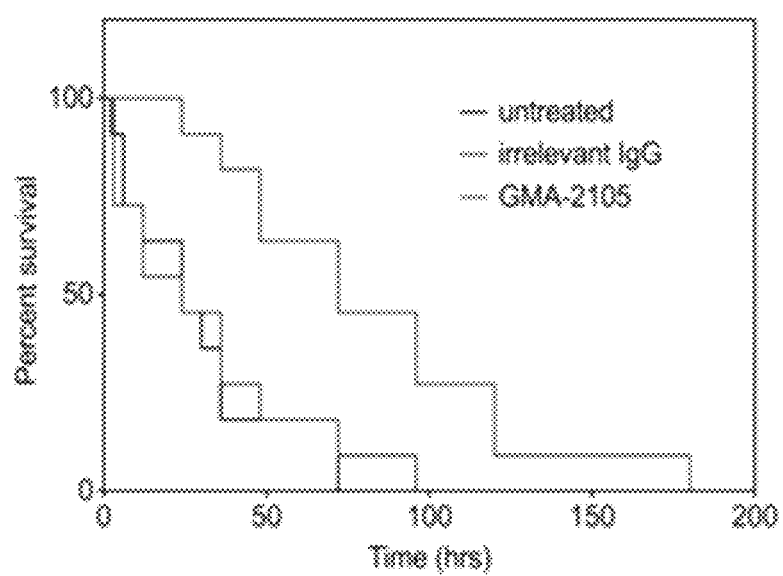
FIG. 22 provides a survival curve demonstrating GMA-2105 promotes survival in a mouse model of *S. aureus* sepsis.

FIG. 22. Survival Curve. C57BL/6 mice were injected intraperitioneal with 120 μg of the mAb against SC(1-10) (GMA-2105) or an isotype-matched irrelevant mAb or PBS buffer with no antibody. After 8-9 hours, treated an untreated mice were injected with $1 \times 10^8$ CFU of *S. aureus* via tail vein and monitored for survival. The anti-SC(1-10) mAb GMA-2105 increased the median survival curves from 24 to 72 h ($p<0.005$ vs. untreated).

Chimeric GMA-2105

Figure 23:
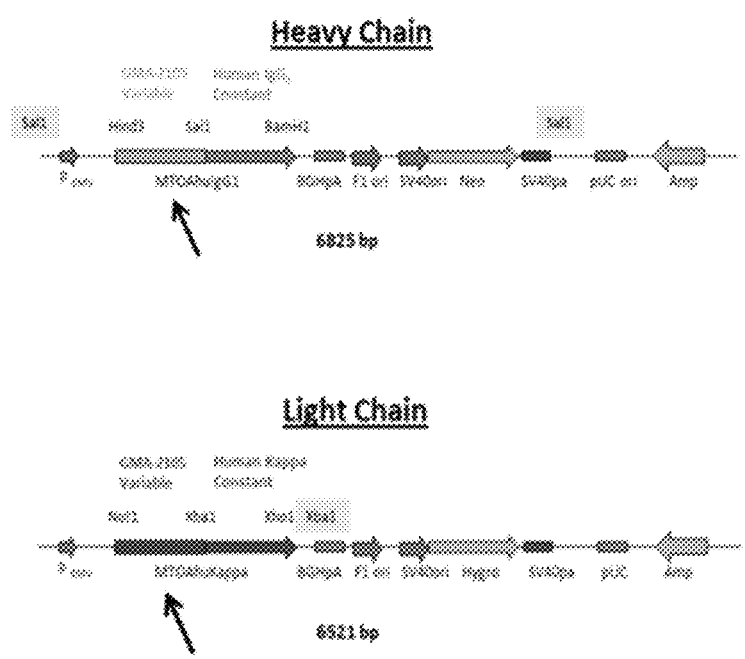
FIG. 23 provides a schematic of an exemplary chimeric GMA-2105 construct.

Chimeric GMA-2105 was made by sequencing cDNA from purified mRNA from GMA-2105 hybridoma cells and using this cDNA sequence to synthesize DNA fragments with appropriate restriction sites at the ends. The DNA segments were inserted into expression vectors containing the human constant regions. FIG. 23 provides a schematic. SEQ ID No. 20 provides an exemplary human IgG$_1$CH1, SEQ ID No. 21 provides an exemplary human IgG$_1$ hinge region; SEQ ID No. 22 provides an exemplary human IgG$_1$ CH2; SEQ ID No. 23 provides an exemplary human IgG$_1$ CH3, SEQ ID No. 24 provides an exemplary human IgG$_1$ kappa light chain constant region.

Figure 24:
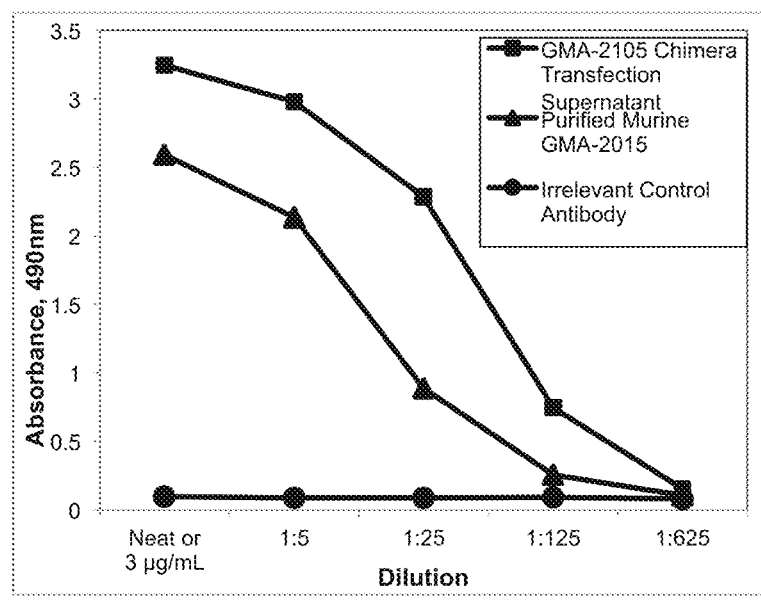
FIG. 24 shows binding of GMA-2105 chimeric antibody in HEK293 cell transfection supernatants to IVTKDYSKES (SEQ ID NO: 9).

The ability of the GMA-2105 antibody chimera to bind staphylocoagulase was tested by analyzing the supernatants of the transfected cells. FIG. 24 provides the results of binding of GMA-2105 chimera in HEK293 cell transfection supernatant to IVTKDYSKES (SEQ ID No. 9) in an ELISA assay. A combination of 55 μg of GMA-2105 heavy chain chimera DNA and 57 μg of GMA-2105 light chain chimera DNA was mixed with 293 fectin and added into $6 \times 10^7$ HEK293 cells in a total volume of 60 mL following Invitrogen's Freestyle 293 Expression system transfection protocol. The cells were incubated at 37 degrees C. with shaking to allow for antibody production and the supernatant was harvested 5 days post transfection. Antibody-antigen complex was detected using a goat anti-human secondary antibody conjugated to horseradish peroxidase for transfection supernatant or goat anti-mouse conjugated to horseradish peroxidase for purified murine GMA-2105 antibody detection. Substrate ortho-phenylenediamine conversion to product was measured at 490 nm using a spectrophotometer. Negative control was purified, irrelevant human IgG.

Figure 25:
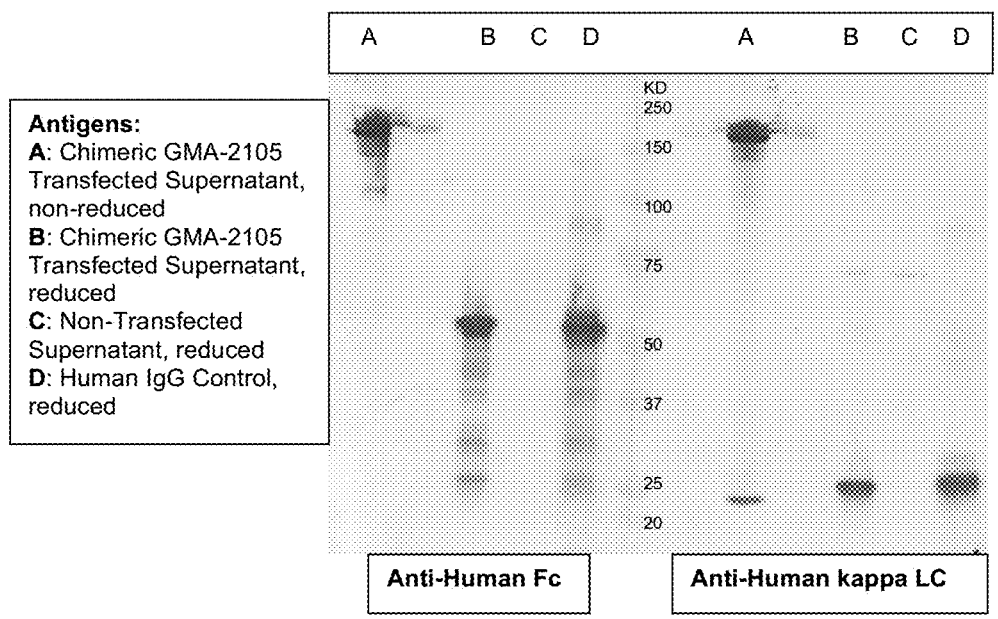
FIG. 25 shows a Western blot detection of human antibody heavy chain Fc and human kappa light chain in HEK293 GMA-2105 chimeric heavy chain and light chain transfected supernatant.
Figure 26:
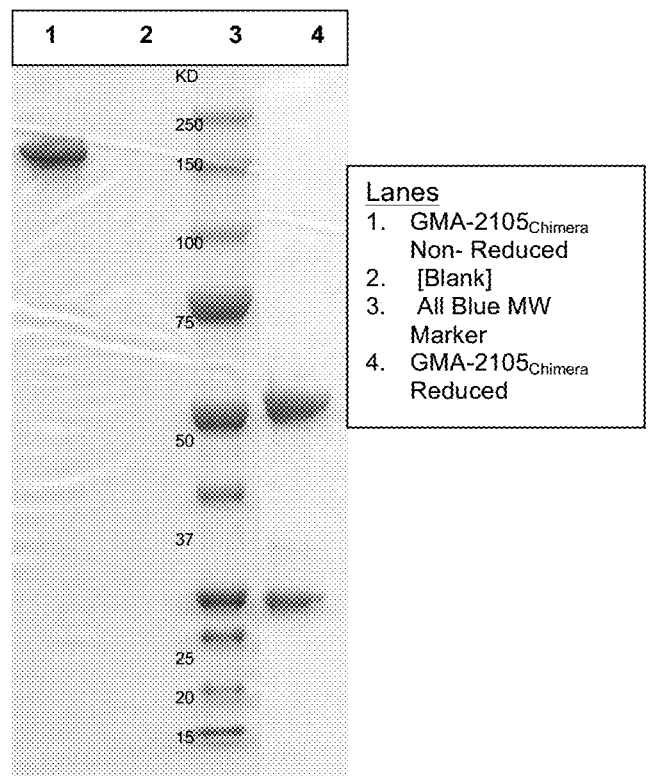
FIG. 26 shows SDS-PAGE analysis of purified GMA-2105 chimera.

The expression of recombinant chimeric GMA-2105 antibodies in supernatants were analyzed with SDS-PAGE, shown as FIG. 25. Detection of human antibody heavy chain Fc and human kappa light chain in HEK293 GMA-2105 chimeric HC and LC transfected supernatant. Supernatants were electrophoresed on NOVEX NUPAGE 4-12% Bis-Tris gel at 200 V followed by electrophoretic transfer to nitrocellulose and blocking with 1% BSA in PBS. Antibody in supernatant was detected using a biotinylated anti-human kappa chain antibody (Vector Laboratories) or biotinylated anti-human IgG, gamma chain specific antibody (Vector Laboratories) followed by avidin peroxidase with chromogenic substrate. Negative control was non-transfected HEK cell supernatant and positive control was human IgG, 0.5 ug load. Lane A: Chimeric GMA-2105 transfected supernatant non-reduced; Lane B: Chimeric GMA-2105 transfected supernatant non-reduced; Lane C: Non-transfected supernatant reduced; Lane D: Human IgG control reduced The purified chimeric GMA-2105 antibodies were analyzed with SDS-PAGE, shown as FIG. 26. An antibody sample of 3 μg was electrophoresed at 200V on a NOVEX NUPAGE 4-12% Bis-Tris gel under reducing and non-reducing conditions. After 1 hour, the gel was removed and incubated in fixative (50% ethanol.water, 7% (v/v) acetic acid) for 1 hour followed by a 2× wash with ddH$_2$O and inubation overnight in Gel Code Blue (Invitrogen) followed by destaining in ddH$_2$O.

Figure 27:
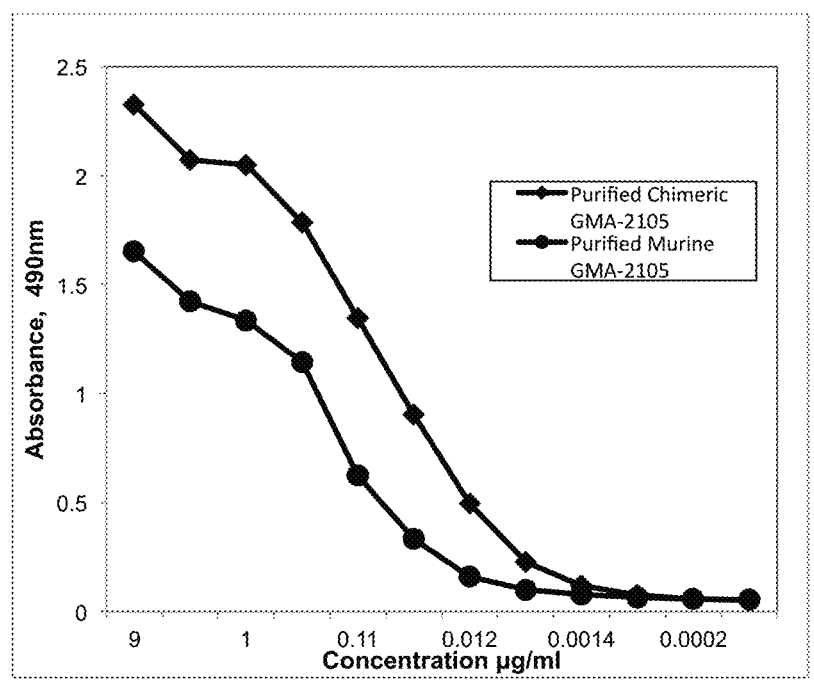
FIG. 27 shows purified chimeric and murine GMA-2105 antibody binding to IVTKDYSKES (SEQ ID NO: 9) in ELISA assay.
Figure 28:
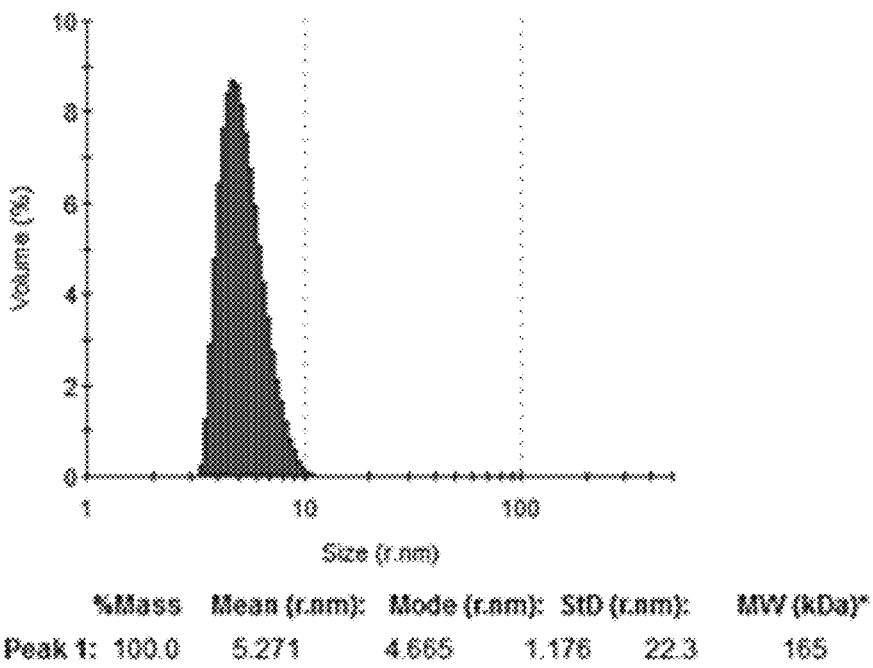
FIG. 28 shows dynamic light scattering of GMA-2105 chimera.

FIG. 27 shows binding of the purified chimeric GMA-2105 against staphylocoagulase. Purified chimeric GMA-2105 and murine GMA-2105 antibody were tested against staphylocoagulase peptide IVTKDYSKES (SEQ ID No.9) in an ELISA assay. The peptide IVTKDYSKES (SEQ ID No. 9) was coated onto wells of 96 well plates at a concentration of 0.5 μg/mL un-conjugated. The plate was washed then blocked with 0.1% BSA followed by addition of antibody dilutions. Antibody-antigen complex was detected using a goat anti-mouse secondary antibody conjugated to horseradish peroxidase or goat anti-human secondary antibody conjugated to horseradish peroxidase. Substrate ortho-phenylene diamine conversion to product was measured at 490 nm using a spectrophotometer The chimeric GMA-2105 antibody was purified by affinity chromatography and analyzed by dynamic light scattering to rule out aggregation. In FIG. 28 dynamic light scattering of GMA-2105 chimera using MALVERN ZETA-SIZER nano S at 25.0° C. The chimeric antibody sample was filtered using a WHATMAN 0.2 µm filter then ~100 uL was loaded into a disposable low-volume sizing cuvette and run using software version 6.20 protein analysis mode.

Figure 29:
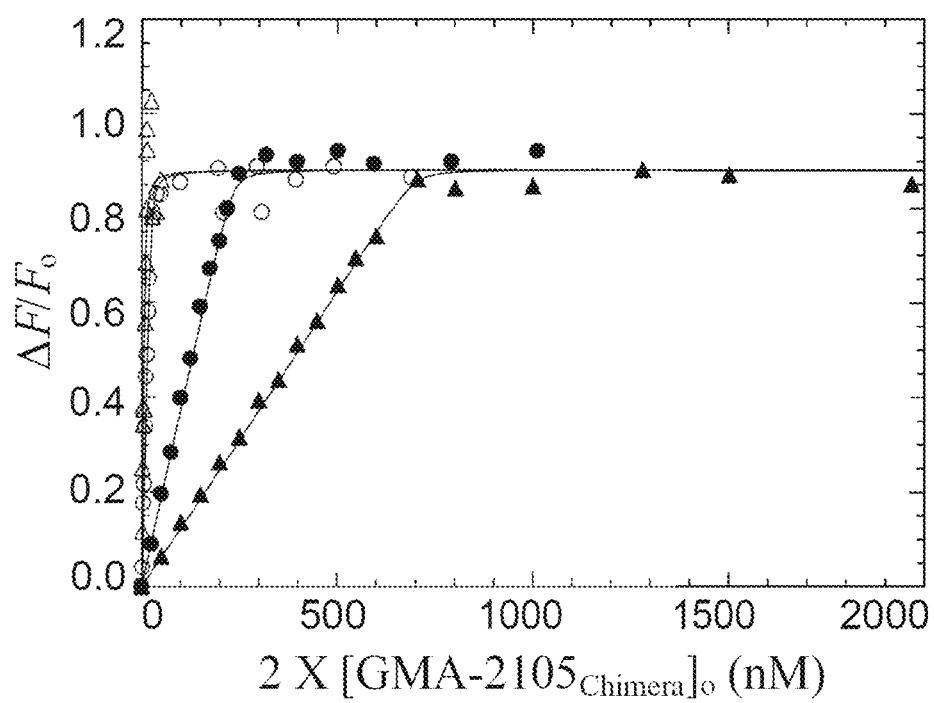
FIG. 29 shows BODIPY-labeled staphylocoagulase fragment SC(1-325) with (S7C) titrated with GMA-2105 chimera in solution.
Figure 31:
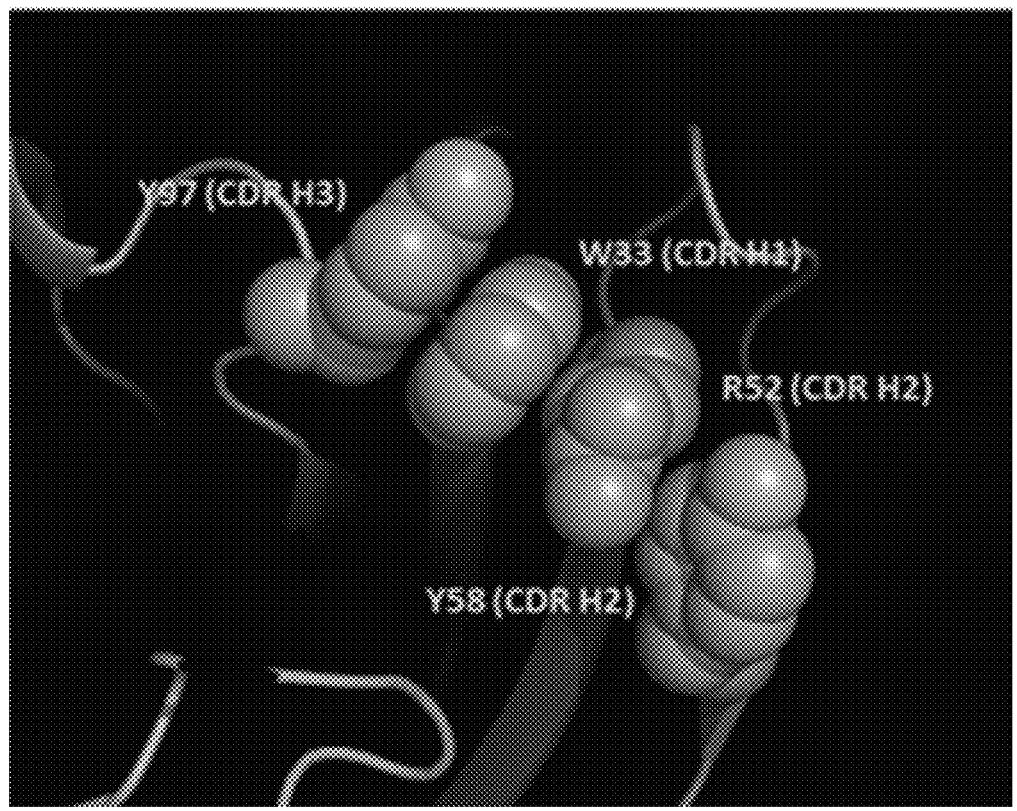
FIG. 31 provides a theoretical model of GMA-2105 light chain SEQ ID No. 8(4-105) and GMA-2105 heavy chain SEQ ID No.:6(4-110).
Figure 32:
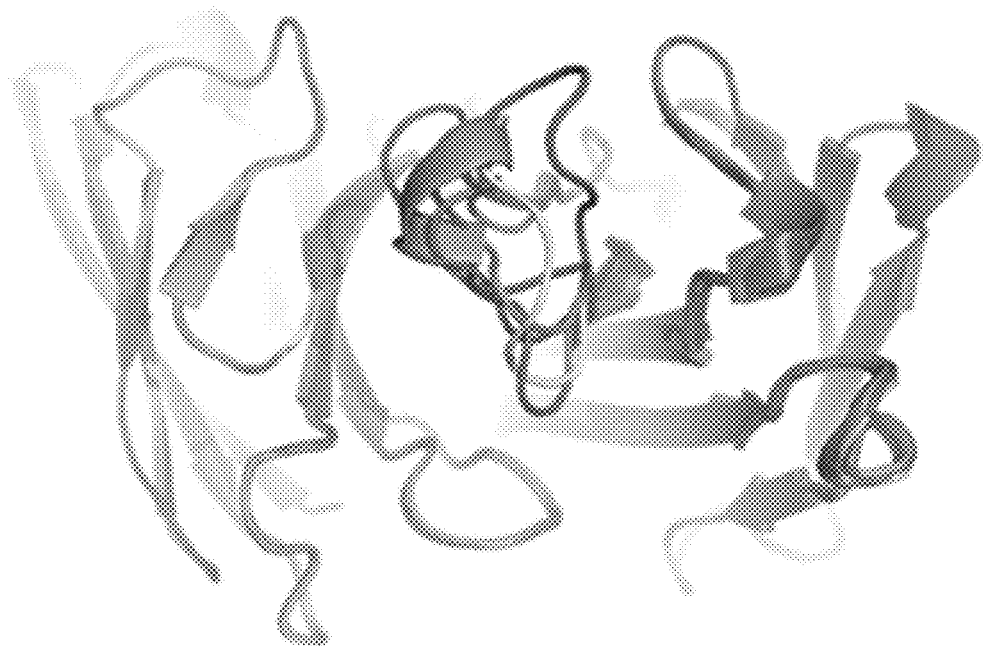
FIG. 32 provides representatives from each of the six clusters formed from the 26 lowest energy GMA-2105 models.
Figure 33:
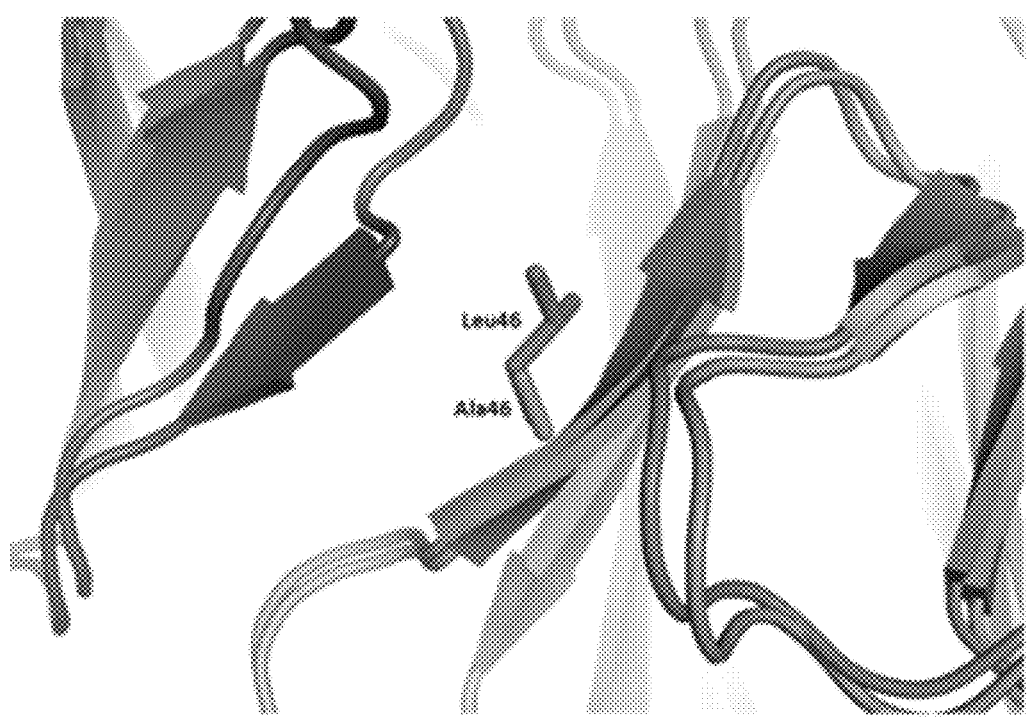
FIG. 33 shows a theoretical model of substitution at GMA-2105 light chain residue 46 (SEQ ID No. 8, residue 46) from alanine to leucine.
Figure 34:
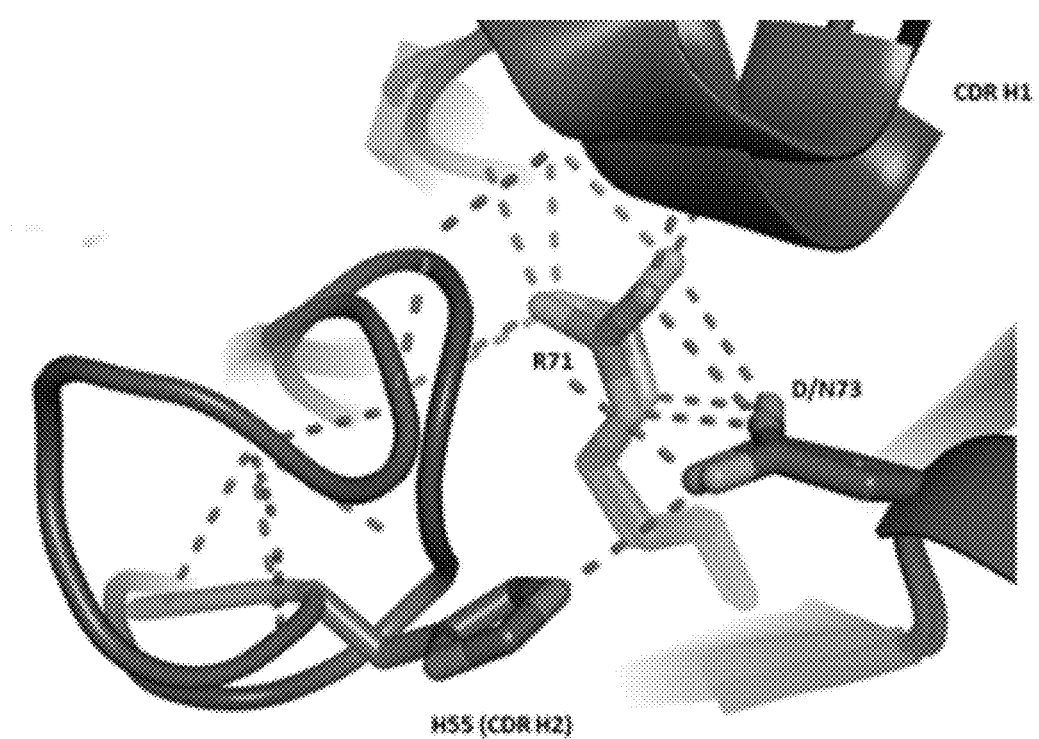
FIG. 34 shows a theoretical model of substituting an asparagine for aspartic acid at heavy chain residue 76 (SEQ ID No.: 6, residue 76).
Figure 35:
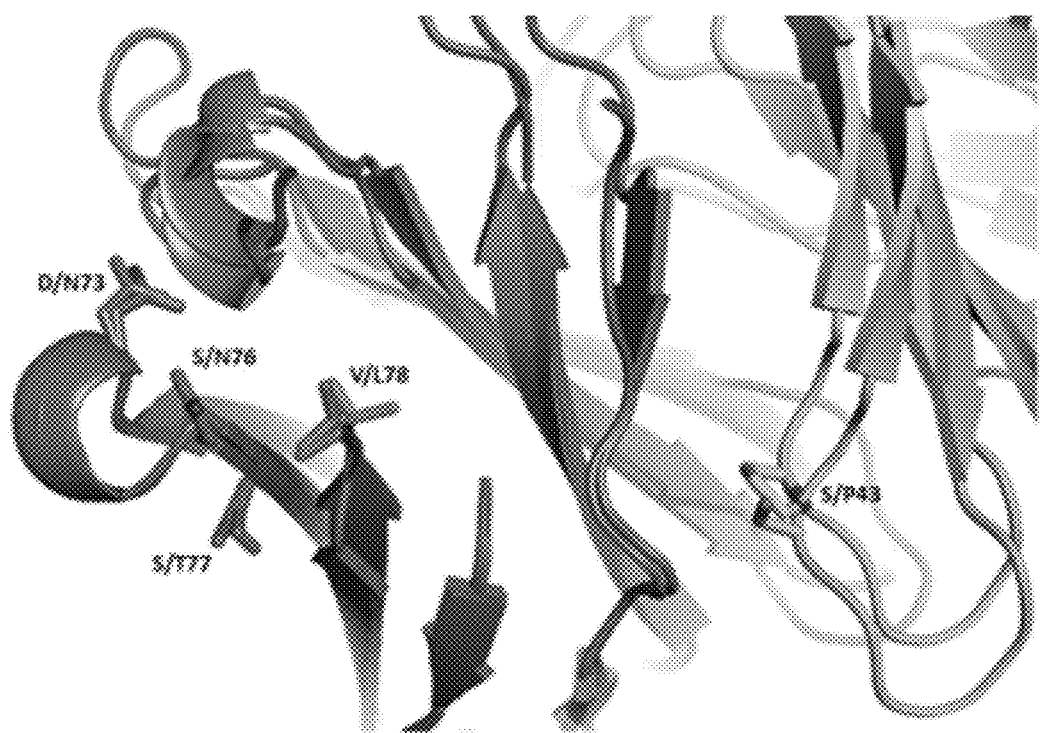
FIG. 35 shows a theoretical model of subsitution of a leucine for a valine at heavy chain residue 81 (SEQ ID No. 6, residue 81).
Figure 36:
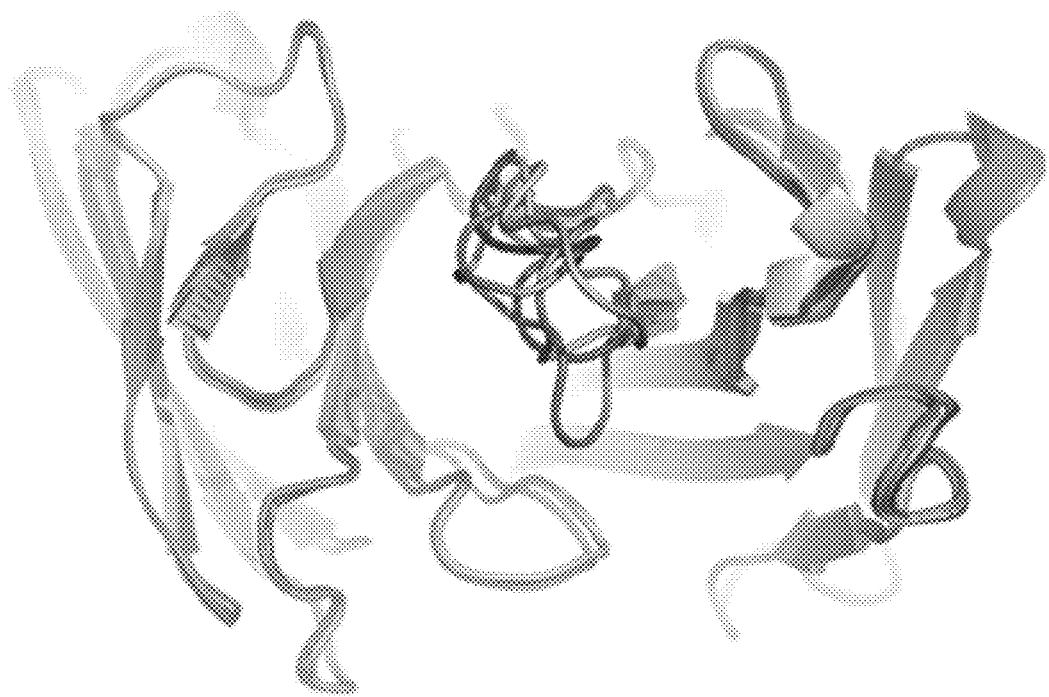
FIG. 36 shows by theoretical model the low energy models of the humanized GMA-2105 sequence.

In FIG. 29, BODIPY®-labeled staphylocoagulase fragment (1-325) at 27 nM (●) and 130 nM (○) titrated with chimeric GMA-2105 in solution in the presence of unlabeled stapylocoagulase fragment (1-246) (▲).

FIG. 30 summarizes the binding characteristics of the murine GMA-2105 and the chimeric GMA-2105. The chimeric antibody bound staphylocoagulase with a $K_D$ of 0.79±0.40 nM and a stoichiometry of 2 mol staphylocoagulase/mol chimeric antibody. The binding characterstics of the chimeric GMA-2105 were essentially identical to values for murine GMA-2105.

Modeling and Construction of Human GMA-2015

Murine antibody sequences were "humanized" to eliminate the human anti-mouse immune response. The first step was formation of a chimeric antibody by grafting the mouse heavy and light chain variable regions onto a human Fc region (described above). A second step was the refinement of the mouse variable regions by substituting specific amino acid residues while maintaining antigen binding of the complementarity determining regions (CDRs) and the supporting scaffold sequences. Human amino acid sequences are either consensus sequences for IgG subgroups, germline sequences, mature human antibody sequences, or sequences with a corresponding x-ray structure (See, e.g., Almagro, et al., Antibody Engineering: Humanization, Affinity Maturation, and Selection Techniques. An Z. editor. Therapeutic Monoclonal Antibodies. Hoboken, N.J.: John Wiley & Son; 2009, incorporated herein by reference).

With the assistance of the Rosetta Design Group, we undertook a structure- and sequence-guided approach to humanization of the GMA-2105 variable region. BLAST analysis of the Protein Data Bank (PDB) for human homologs of GMA-2105 identified a human germline antibody (B3/3-23) as a suitable scaffold, with an available crystal structure (PDB ID:3QOS), as a recipient for the GMA-2105 CDRs (Seq ID Nos. 10-15). A small ensemble of models for the GMA-2105 variable region resulted from 3000 folding simulations. The ensemble was analyzed to determine GMA-2105 scaffold amino acids that might effect CDR conformation and hence antigen binding. After grafting the GMA-2105 CDRs (SEQ ID Nos.: 10-15) into B3/3-23, further simulations were conducted to assess the effect of back-mutations.

FIG. 31 provides a theoretical model of GMA-2105 light chain SEQ ID No.:8, residues 4-105) and GMA-2105 heavy chain (SEQ ID No. 6, residues 4-110) using RosettaAntibody software. Model shows Tr-stacking interacions among the complementarity determining regions and aromatic residues that are well packed.

FIG. 32 provides representatives from each of the 6 clusters formed from the 26 lowest energy GMA-2105 models. A feature in the dominant cluster is π-stacking interacions among residues W33, R52, Y58, and Y97 of the GMA-2105 heavy chain (SEQ ID No. 6).

FIG. 33 shows that substitution at GMA-2105 light chain residue 46 (SEQ ID No. 8, residue 46) from alanine to leucine in the human framework may effect inter-chain orientation as this residue lies at the light-heavy chain interface.

FIG. 34 shows that substituting an asparagine for aspartic acid at heavy chain residue 76 (SEQ ID No.: 6, residue 76) may affect the folding of the heavy chain. D76 (SEQ ID No.: 6, residue 76) may form a salt bridge with residue H58 of heavy chain CDR 2 (SEQ ID No.: 6, residue 58 and SEQ ID. No.:14, residue 8) and residue R74 (SEQ ID No.: 6, residue 74) of the framework. The subsittution of asparagine at position 76 (SEQ ID No.: 6, residue 76) forms a hydrogen bond to CDR 2 (SEQ ID No.: 10) of the heavy chain in the human model, but it is unclear what effect other differences in the sequence would make on this interaction. In a variation, a humanization of GMA-2105 sequence may retain an aspartic acid at position 76 (SEQ ID No.: 6, residue 76). On FIG. 34, the numeric indicators are shifted by 3. SEQ ID No.: 6, residue 76 is indicated by D/N73 on FIG. 34. SEQ ID No.: 6, residue 58 is indicated by H55 on FIG. 34. SEQ ID No.: 6, residue 74 is indicated by R71 on FIG. 34.

FIG. 35, subsitution of a leucine for a valine at heavy chain residue 81 (SEQ ID No. 6, residue 81) may impact the the van der Waals contact between heavy chain residue 81 and heavy chain CDR 1 residue F 29 (SEQ ID No. 6, residue 29 and SEQ ID No. 13, residue 4). Substitutions of (N for S) at heavy chain position 79 (SEQ ID No. 6, residue 79), substitution (T for S) at heavy chain position 80 (SEQ ID. No. 6, residue 80) and substitution (P for S) at light chain position 43 (SEQ ID. No. 8, residue 43) may also disrupt the contact beween heavy chain residue F29 and the H55-D73 salt bridge. In a variation, a humanization of GMA-2105 may may retained the mouse residue at at least one of positions 43, 79, 80, and 81. On FIG. 35, the number indicators are shifted in some instances. Therefore, SEQ ID No. 6, position 81 is indicated as V/L78 on FIG. 35. SEQ ID No. 6, residue 79 is indicated as S/N76, on FIG. 35. SEQ ID No. 6, residue 80 is indicated as S/T77, on FIG. 35.

FIG. 36, the low energy models of the humanized GMA-2105 sequence. Twenty three models grouped into five clusters based on the conformation of heavy chain CDR3 (SEQ ID No.: 15). The largest of the five clusters (16/23) clustered with the largest murine GMA-2105 cluster.

Therapeutic Applications

Monoclonal antibodies (mAbs) that specifically inhibit staphylocoagulase functions are less likely than anti-coagulants to have off-target adverse effects and would be a significant step forward.

The monoclonal antibodies disclosed herein are usable as inhibitors of staphylocoagulase.

The antibodies provided may also be formed into suitable pharmaceutical compositions, for administration to a human or animal patient in order to treat or prevent an infection caused by staphylococcal bacteria. Pharmaceutical compositions containing the antibodies provided, variations, and/or effective fragments thereof, may be formulated in combination with any suitable pharmaceutical vehicle, excipient or carrier that would commonly be used in this art, including such conventional materials for this purpose, e.g., saline, dextrose, water, glycerol, ethanol, other therapeutic compounds, and combinations thereof. The particular vehicle, excipient or carrier used will vary depending on the patient and the patient's condition, and a variety of modes of administration would be suitable for the compositions, as would be recognized by one of ordinary skill in this art. Suitable methods of administration of any pharmaceutical composition disclosed in this application include, but are not limited to, topical, oral, anal, vaginal, intravenous, intraperitoneal, intramuscular, subcutaneous, intranasal and intradermal administration.

If topical administration is desired, the composition may be formulated as needed in a suitable form, e.g., an ointment, cream, gel, lotion, drops (such as eye drops and ear drops), or solution (such as mouthwash). Wound or surgical dressings, sutures and aerosols may be impregnated with the composition. The composition may contain conventional additives, such as preservatives, solvents to promote penetration, and emollients. Topical formulations may also contain conventional carriers such as cream or ointment bases, ethanol, or others.

The antibody compositions provided will thus be useful for interfering with, modulating, or inhibiting binding interactions between the staphylococcal-secreted staphylocoagulase protein and its ligand protein prothrombin in blood and tissues, and will thus have particular applicability in developing compositions and methods of preventing or treating staphylococcal infection, and in inhibiting the activation of prothrom bin.

Methods are provided for preventing or treating a staphylococcal infection which comprise administering an effective amount of the monoclonal antibody as described above in amounts effective to treat or prevent the infection. In addition, these monoclonal antibodies (in various forms including murine, chimeric, humanized sequences, and F(ab) fragments), and have been shown to have high affinity in binding of staphylocoagulase secreted by staphylococcal bacteria, and effective in treating or preventing infection from staph bacteria such as *S. aureus*. This tendency is supported by the mouse survival data provided herein. Further, as demonstrated by the inhibition studies, these monoclonals will be useful in inhibiting *S. aureus* from activating host coagulation mechanisms, e.g., those involved in development of AIE.

Accordingly, administration of the antibodies disclosed herein in any of the conventional ways described above (e.g., topical, parenteral, intramuscular, etc.), may provide an extremely useful method of treating or preventing staphylococcal infections in human or animal patients. By effective amount is meant that level of use, such as of an antibody titer, that will be sufficient to either prevent adherence of the bacteria, to inhibit binding of staph bacteria to host cells and thus be useful in the treatment or prevention of a staph infection. As would be recognized by one of ordinary skill in this art, the level of antibody titer needed to be effective in treating or preventing staphylococcal infection will vary depending on the nature and condition of the patient, and/or the severity of the pre-existing staphylococcal infection.

In addition to the use of disclosed antibodies and degenerative or homologs thereof to treat or prevent *S. aureus* infection as described above, we contemplate the use of these antibodies in a variety of ways, including the detection of the presence of *S. aureus* to diagnose a staph infection, whether in a patient or on medical equipment, implants or prosthetics which may also become infected. For example, a method of detecting the presence of staph infections involves the steps of obtaining a sample suspected of being infected by one or more staphylococcal bacteria species or strains, such as a sample taken from an individual, for example, from one's blood, saliva, tissues, bone, muscle, cartilage, or skin. The cells can then be lysed, and the DNA extracted, precipitated and amplified. Following isolation of the sample, diagnostic assays utilizing the disclosed antibodies may be carried out to detect the presence of *S. aureus*, and such assay techniques for determining such presence in a sample are well known to those skilled in the art and include methods such as radioimmunoassay, Western blot analysis and ELISA assays. A method of diagnosing an *S. aureus* infection is contemplated wherein a sample suspected of being infected with *S. aureus* infection has added to it the monoclonal antibody described herein, and *S. aureus* is indicated by antibody binding to the staphylocoagulase proteins in the sample.

Accordingly, disclosed antibodies may be used for the specific detection or diagnosis of staphylococcal proteins, for the prevention of infection from staph bacteria, for the treatment of an ongoing infection, or for use as research tools. The term "antibodies" as used herein includes monoclonal, polyclonal, chimeric, single chain, bispecific, simianized, and humanized or primatized antibodies as well as F(ab) fragments, such as those fragments which maintain the binding specificity of the antibodies to the staphylocoagulase proteins, including the products of an F(ab) immunoglobulin expression library. Accordingly, we contemplate the use of single chains such as the variable heavy and light chains of the antibodies as will be set forth below. Generation of any of these types of antibodies or antibody fragments is well known to those skilled in the art. In the present case, monoclonal antibodies to staphylocoagulase proteins have been generated against N-terminal staphylocoagulase protein and have been isolated and shown to have high affinity to *S. aureus*. Moreover, the monoclonals provided have been shown to recognize a high number of strains, on an equivalent level to that recognize by polyclonal antibodies to staphylocoagulase, and thus can be used effectively in methods to protect against staphylococcal infection or treat same.

Antibodies to staphylocoagulase as described above may also be used in production facilities or laboratories to isolate additional quantities of the proteins, such as by affinity chromatography. For example, the antibodies may also be utilized to isolate additional amounts of the staphylocoagulase proteins or their active fragments.

The isolated antibodies provided herein, or active fragments thereof, may also be utilized in the development of vaccines for passive immunization against staph infections, Further, when administered as pharmaceutical composition to a wound or used to coat medical devices or polymeric biomaterials in vitro and in vivo, the antibodies may be useful in those cases where there is a previous staph infection because of the ability of this antibody to further restrict and inhibit *S. aureus* staphylocoagulase binding to prothrom bin and thus limit the extent of the infection. In addition, the antibody may be modified so that, in certain instances, to reduce the immunogenicity in the patient to whom it is administered. For example, if the patient is a human, the antibody may be "humanized" by transplanting the complementarity determining regions (CDR's) (e.g., SEQ ID Nos. 10-15) of the hybridoma-derived antibody into a human monoclonal antibody as described, e.g., by Jones et al., *Nature* 321:522-525 (1986) or Tempest et al. *Biotechnology* 9:266-273 (1991) and demonstrated herein. They may also be "veneered" by changing the surface exposed murine framework residues in the immunoglobulin variable regions to mimic a homologous human framework counterpart as described, e.g., by Padlan, *Molecular Imm.* 28:489-498 (1991) and U.S. Pat. No. 6,797,492, all of these references incorporated herein by reference. Even further, when so desired, the disclosed monoclonal antibodies may be administered in conjunction with a suitable antibiotic to further enhance the ability of the present compositions to fight bacterial infections.

The antibodies may also be used as a passive vaccine which will be useful in providing suitable antibodies to treat or prevent a staphylococcal infection. As would be recognized by one skilled in this art, a vaccine may be packaged for administration in a number of suitable ways, such as by parenteral (i.e., intramuscular, intradermal or subcutaneous) administration or nasopharyngeal (i.e., intranasal) administration. One such mode is where the vaccine is injected intramuscularly, e.g., into the deltoid muscle, however, the particular mode of administration will depend on the nature of the bacterial infection to be dealt with and the condition of the patient. The vaccine may be combined with a pharmaceutically acceptable carrier to facilitate administration, and the carrier is usually water or a buffered saline, with or without a preservative. The vaccine may be lyophilized for resuspension at the time of administration or in solution.

While "SC" and "staphylocoagulase" is used throughout, it is contemplated that the disclosed monoclonal antibodies are also useful against homologs or degenerate versions of SC. Similarly, while DNA and amino acid sequences are disclosed, it is contemplated that the claims cover the disclosed sequences as well as substantially similar sequences.

Two DNA sequences are "substantially similar" when approximately 70% or more (e.g., at least about 80%, at least about 89%, 90%, 91%, 92%, 93%, 94%, 95%, 96%, 97%, 98%, 99%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., *Molecular Cloning: A Laboratory Manual*, 1982; DNA Cloning, Vols. I & II, supra; *Nucleic Acid Hybridization*, [B. D. Hames & S. J. Higgins eds. (1985)].

By "substantially similar" is further meant a DNA sequence which, by virtue of the degeneracy of the genetic code, is not identical with that shown in any of the sequences disclosed, but which still encodes the same amino acid sequence; or a DNA sequence which encodes a different amino acid sequence that retains the activities of the proteins, either because one amino acid is replaced with a similar amino acid, or because the change (whether it be substitution, deletion or insertion) does not affect the active site of the protein.

Two amino acid sequences or two nucleic acid sequences are "substantially similar" when approximately 70% or more (e.g., at least about 80%, at least about 89%, 90%, 91%, 92%, 93%, 94%, 95%, 96%, 97%, 98%, 99%) of the amino acids match over the defined length of the sequences, As demonstrated by evidence herein, modification and changes may be made in the structure of the peptides and DNA segments which encode them and still obtain a functional molecule that encodes a protein or peptide with desirable characteristics. The changing the amino acids of a protein may be used to create an equivalent, or even an improved, second generation molecule.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions, or corresponding DNA sequences which encode said peptides without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, *J. Mol Biol,* 157(1):105-132, 1982.

It is known in the art that certain amino acids may be substituted by other amino acids having a similar hydropathic index or score and still result in a protein with similar biological activity, i.e., still obtain a biological functionally equivalent protein. In making such changes, there is a general trend toward substitution of amino acids whose hydropathic indices are within about ±0.5 to about ±2. It is also understood in the art that the substitution of like amino acids can be made effectively on the basis of hydrophilicity. For example, local average hydrophilicity of a protein, as governed by the hydrophilicity of its adjacent amino acids, may correlate with a biological property of the protein.

It is understood that an amino acid can be substituted for another having a similar hydrophilicity value and still obtain a biologically equivalent, and in particular, an immunologically equivalent protein.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include but are not limited to: arginine and lysine; glutamate and aspartate; serine and threonine; glutamine and asparagine; and valine, leucine and isoleucine.

The polypeptides can be can be chemically synthesized. The synthetic polypeptides are prepared using the well known techniques such as but not limited to solid phase, liquid phase, or peptide condensation techniques, or any combination thereof, and can include natural and unnatural amino acids.

ATCC Deposit

On Aug. 14, 2013, a deposit of biological material was made in a depository affording permanence of the deposit and ready accessibility of thereto by the public if a patent is granted. Specifically, a deposit of biological material has been made with the American Type Culture Collection (ATCC), 10801 University Boulevard, Manassas, Va., 20110, United States of America.

The deposited material is a hybridoma cell line derived from BALB/c mouse (*Mus musculus*) spleen cells. The cell lines express staphcoagulase GMA-2105, clone 2A1.5H4.2D3.137. The ATCC assigned the deposit accession number ATCC PTA-120537. All restrictions on the availability to the public of the material so deposited will be irrevocably removed upon the granting of the patent. The materials have been deposited under conditions that access to the materials will be available during the pendency of the patent application to one determined by the Commissioner to be entitled thereto under 37 C.F.R.1.14 and 35 U.S.C. § 122.

The deposited materials will be maintained with all the care necessary to keep it viable and uncontaminated for a period of at least five years after the most recent request for the furnishing of a sample of the deposited material, and in any case, for a period of at least thirty (30) years after the date of deposit or for the enforceable life of the patent, whichever period is longer. It should be understood that the availability of a deposit does not constitute a license to practice the subject invention in derogation of patent rights granted by government action.

The invention is not limited to the embodiments illustrated and described, as it also covers all equivalent implementations insofar as they do not depart form the spirit of the invention. Further, the invention is not yet limited to the combination of features as described herein but may be defined by any other combination of all of the individual features disclosed. Further, the invention is not yet limited to the sequence of method steps as described herein but may be defined by any other combination or order the steps disclosed. Any person skilled in the art of will recognize from the previous detailed description and from the figures and claims that modifications could be made to the disclosed embodiments of the invention without departing from the scope of the invention.

The invention claimed is:

1. A method of treating a staphylococcal infection, said method comprising using an antibody or antigen-binding fragment thereof which binds an epitope of staphylocoagulase peptide that is within SEQ ID. No: 2 and which comprises the following CDRS:

| | | |
|---|---|---|
| CDRL1: | QNVDIY | (SEQ ID NO: 10) |
| CDRL2: | SAS | (SEQ ID NO.: 11) |
| CDRL3: | QQYNNYPYT | (SEQ ID NO: 12) |
| CDRH1: | GFTFSDAW | (SEQ ID NO: 13) |
| CDRH2: | IRTKANNHAT | (SEQ ID NO: 14) |
| CDRH3: | CTNVYYGNNDVKDY | (SEQ ID NO: 15). |

2. The method of claim 1, wherein the epitope that binds the isolated antibody is within residues 1-10 of SEQ ID No: 2.

3. The method of claim 1, wherein the isolated monoclonal antibody or antigen-binding fragment thereof is produced from a hybridoma cell having accession number PTA-120537.

4. The method of claim 1, wherein the isolated monoclonal antibody or antigen-binding fragment thereof comprises a $V_H$ region having at least 95% identity with SEQ ID NO: 6 and a $V_L$ region having at least 95% identity with SEQ ID NO: 8.

5. The method of claim 1, wherein the isolated monoclonal antibody or antigen-binding fragment thereof is humanized.

* * * * *